United States Patent
Ai et al.

(10) Patent No.: US 9,664,697 B2
(45) Date of Patent: May 30, 2017

(54) GREEN-TO-RED PHOTO-CONVERTIBLE FLUORESCENT CALCIUM INDICATOR

(71) Applicant: New York University, New York, NY (US)

(72) Inventors: Minrong Ai, Zionsville, IN (US); Greg Seong-Bae Suh, New York, NY (US)

(73) Assignee: New York University, New York, NY (US)

( * ) Notice: Subject to any disclaimer, the term of this patent is extended or adjusted under 35 U.S.C. 154(b) by 101 days.

(21) Appl. No.: 14/622,025

(22) Filed: Feb. 13, 2015

(65) Prior Publication Data

US 2015/0226755 A1 Aug. 13, 2015

Related U.S. Application Data

(60) Provisional application No. 61/939,373, filed on Feb. 13, 2014.

(51) Int. Cl.
*G01N 33/84* (2006.01)
*G01N 33/58* (2006.01)
*G01N 21/64* (2006.01)

(52) U.S. Cl.
CPC ......... *G01N 33/84* (2013.01); *G01N 21/6486* (2013.01); *G01N 33/582* (2013.01); *G01N 2333/4727* (2013.01); *G01N 2500/10* (2013.01)

(58) Field of Classification Search
CPC .. G01N 33/84; G01N 33/582; G01N 21/6486; G01N 2500/10; G01N 2333/4227
See application file for complete search history.

(56) References Cited

PUBLICATIONS

Wiedenmann et al., EosFP, a fluorescent marker protein with UV-inducible green-to-red fluorescence conversion., Proc Natl Acad Sci U S A. (2004), vol. 101(45), pp. 15905-15910.*

Ando et al., an optical marker based on the UV-induced green-to-red photoconversion of a fluorescent protein., Proc Natl Acad Sci U S A. (2002), vol. 99(20), pp. 12651-12656.*

Nienhaus et al., Structural basis for photo-induced protein cleavage and green-to-red conversion of fluorescent protein EosFP., Proc Natl Acad Sci U S A. (2005), vol. 102(26), pp. 9156-9159.*

Tian et al., Imaging neural activity in worms, flies and mice with improved GCaMP calcium indicators., Nat Methods. (2009), vol. 6(12), pp. 875-881.*

Baird et al., Circular permutation and receptor insertion within green fluorescent proteins, Proc. Natl. Acad. Sci. USA vol. 96, pp. 11241-11246, Sep. 1999.

Zhao et al., An Expanded Palette of Genetically Encoded Ca2+ Indicators, Science vol. 333, Sep. 30, 2011.

Weidenmann et al., EosFP, a fluorescent marker protein with UV-inducible green-to-red fluorescence conversion, Proc. Natl. Acad. Sci. USA, vol. 101(45), Nov. 9, 2004.

(Continued)

*Primary Examiner* — Alexander Kim
(74) *Attorney, Agent, or Firm* — Hodgson Russ LLP

(57) ABSTRACT

Provided are methods of selectively labeling cells by introduction of circularly permutated GCaMP molecules which exhibit photoconversion from green to red fluorescence when exposed to blue light. The intensity red fluorescence can also be used as a calcium indicator.

12 Claims, 10 Drawing Sheets

(9 of 10 Drawing Sheet(s) Filed in Color)

(56) References Cited

PUBLICATIONS

Ando et al., An optical marker based on the UV-induced green-to-red photoconversion of a fluorescent protein, Proc. Natl. Acad. Sci. USA, vol. 99(20), Oct. 2, 2002.

Gurskaya et al., Engineering of a monomeric green-to-red photoactivatable fluorescent protein induced by blue light, Nature Biotechnology 24, pp. 461-465, Mar. 19, 2006.

Labas et al., Diversity and evolution of the green fluorescent protein family, Proc. Natl. Acad. Sci. USA, vol. 99(7), pp. 4256-4261, Apr. 2, 2002.

Tsutsui et al., Semi-rational engineering of a coral fluorescent protein into an efficient highlighter, EMBO, vol. 6(3):233-238, Mar. 2005.

Habuchi et al., mKikGR, a Monomeric Photoswitchable Fluorescent Protein, PLoS ONE 3(12): e3944, Dec. 15, 2008.

Mizuno et al., Photo-Induced Peptide Cleavage in the Green-to-Red Conversion of a Fluorescent Protein, Molecular Cell, vol. 12, Issue 4, pp. 1051-1058, Oct. 2003.

Elowitz et al., Photoactivation turns green fluorescent protein red, Current Biology, vol. 7, Issue 10, pp. 809-812, Oct. 1, 1997.

Sawin et al., Photoactivation of green fluorescent protein, Current Biology, vol. 7, Issue 10, pp. R606-R607, Oct. 1, 1997.

Jakobs et al., Photoconversion of matrix targeted GFP enables analysis of continuity and intermixing of the mitochondrial lumen, FEBS Letters, vol. 554(1-2), pp. 194-200, Nov. 6, 2003.

Takahashi et al., In vivo oxygen imaging using green fluorescent protein, American Journal of Physiology—Cell Physiology, vol. 291 No. 4, pp. C781-C787, Oct. 1, 2006.

Bogdanov et al., Green fluorescent proteins are light-induced electron donors, Nature Chemical Biology 5, pp. 459-461 (2009).

Saha et al., Light driven ultrafast electron transfer in oxidative redding of Green Fluorescent Proteins, Scientific Reports 3, Article No. 1580, Apr. 3, 2013.

\* cited by examiner

Figure 2A
Figure 2B
Figure 2C
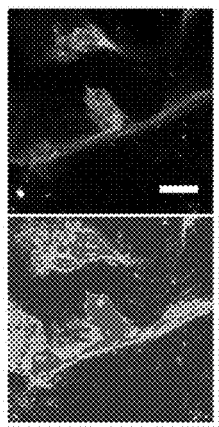
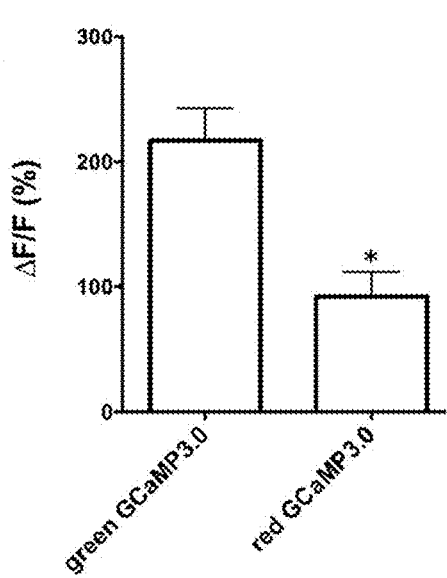
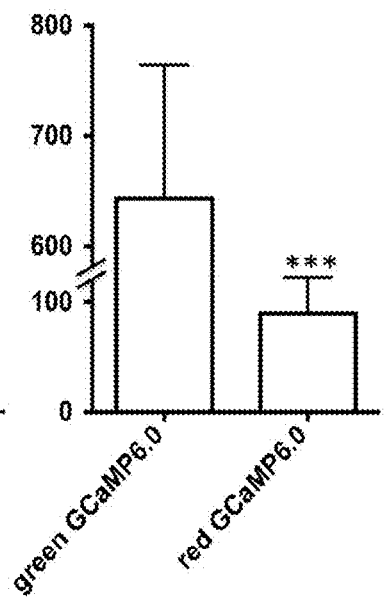

Figure 3A
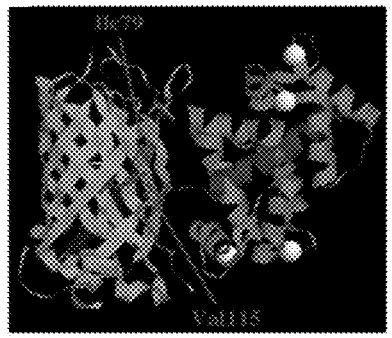
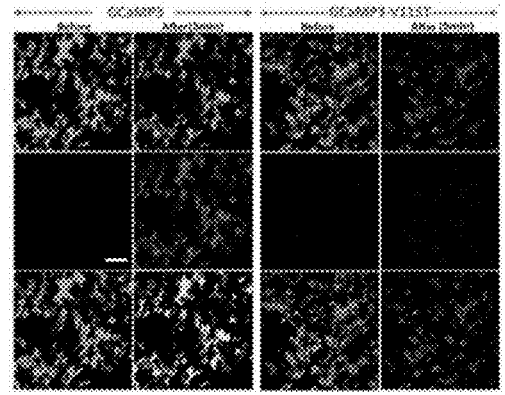
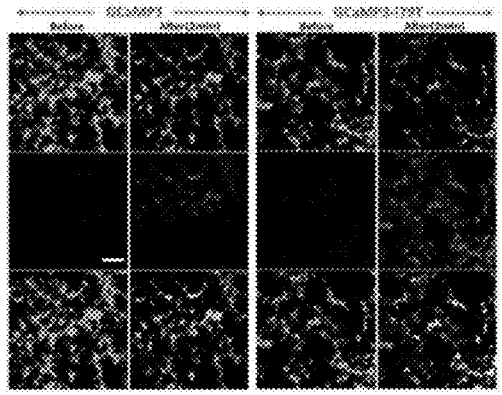
Figure 3B
Figure 3C

SEQUENCE LISTING

<160> NUMBER OF SEQ ID NOS: 10

<210> SEQ ID NO 1
<211> LENGTH: 1353
<212> TYPE: DNA
<213> ORGANISM: Artificial Sequence
<220> FEATURE:
<223> OTHER INFORMATION: Circularly permutated DNA

<400> SEQUENCE: 1

```
atgggttctc atcatcatca tcatcatggt atggctagca tgactggtgg acagcaaatg      60
ggtcgggatc tgtacgacga tgacgataag gatctcgcca ccatggtcga ctcatcacgt     120
cgtaagtgga ataagacagg tcacgcagtc agagctatag gtcggctgag ctcactcgag     180
aacgtctata tcaaggccga caagcagaag aacggcatca aggcgaactt caagatccgc     240
cacaacatcg aggacggcgg cgtgcagctc gcctaccact accagcagaa cacccccatc     300
ggcgacggcc ccgtgctgct gcccgacaac cactacctga gcgtgcagtc caaactttcg     360
aaagacccca cgagaagcg cgatcacatg gtcctgctgg agttcgtgac cgccgccggg     420
atcactctcg gcatggacga gctgtacaag ggcggtaccg gagggagcat ggtgagcaag     480
ggcgaggagc tgttcaccgg ggtggtgccc atcctggtcg agctggacgg cgacgtaaac     540
ggccacaagt tcagcgtgtc cggcgagggt gagggcgatg ccacctacgg caagctgacc     600
ctgaagttca tctgcaccac cggcaagctg cccgtgccct ggcccaccct cgtgaccacc     660
ctgacctacg gcgtgcagtg cttcagccgc taccccgacc acatgaagca gcacgacttc     720
ttcaagtccg ccatgcccga aggctacatc caggagcgca ccatcttctt caaggacgac     780
ggcaactaca agacccgcgc cgaggtgaag ttcgagggcg acaccctggt gaaccgcatc     840
gagctgaagg gcatcgactt caaggaggac ggcaacatcc tggggcacaa gctggagtac     900
aacacgcgtg accaactgac tgaagagcag atcgcagaat taaagaggc tttctcccta     960 tttgacaagg acggggatgg gacaataaca accaaggagc tggggacggt gatgcggtct    1020
ctggggcaga accccacaga agcagagctg caggacatga tcaatgaagt agatgccgac    1080
ggtgacggca caatcgactt ccctgagttc ctgacaatga tggcaagaaa aatgaaagac    1140
acagacagtg aagaagaaat tagagaagcg ttccgtgtgt tgataagga tggcaatggc    1200 tacatcagtg cagcagagct tcgccacgtg atgacaaacc ttggagagaa gttaacagat    1260
gaagaggttg atgaaatgat cagggaagca gacatcgatg gggatggtca ggtaaactac    1320
gaagagtttg tacaaatgat gacagcgaag tga                                 1353
```

<210> SEQ ID NO 2

```
<211> LENGTH: 450
<212> TYPE: PRT
<213> ORGANISM: Artificial Sequence
<220> FEATURE:
<223> OTHER INFORMATION: Circularly permutated protein

<400> SEQUENCE: 2

Met Gly Ser His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
    50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
    130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
    210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Thr Arg Asp
    290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asp Gly Thr Ile Asp Phe Pro
        355                 360                 365

Glu Phe Leu Thr Met Met Ala Arg Lys Met Lys Asp Thr Asp Ser Glu
    370                 375                 380
```

```
Glu Ile Arg Glu Ala Phe Arg Val Phe Asp Lys Asp Gly Asn Gly
385             390                 395                 400

Tyr Ile Ser Ala Ala Glu Leu Arg His Val Met Thr Asn Leu Gly Glu
            405                 410                 415

Lys Leu Thr Asp Glu Glu Val Asp Glu Met Ile Arg Glu Ala Asp Ile
        420                 425                 430

Asp Gly Asp Gly Gln Val Asn Tyr Glu Glu Phe Val Gln Met Met Thr
        435                 440                 445

Ala Lys
    450

<210> SEQ ID NO 3
<211> LENGTH: 1353
<212> TYPE: DNA
<213> ORGANISM: Artificial Sequence
<220> FEATURE:
<223> OTHER INFORMATION: Circularly permutated DNA

<400> SEQUENCE: 3
atgggttctc atcatcatca tcatcatggt atggctagca tgactggtgg acagcaaatg      60
ggtcgggatc tgtacgacga tgacgataag gatctcgcca ccatggtcga ctcatcacgt     120
cgtaagtgga ataagacagg tcacgcagtc agagctatag gtcggctgag ctcactcgag     180
aacgtctata tcaaggccga caagcagaag aacggcatca aggcgaactt caagatccgc     240
cacaacatcg aggacggcgg cgtgcagctc gcctaccact accagcagaa caccccccatc    300 ggcgacggcc ccgtgctgct gcccgacaac cactacctga gcgtgcagtc caaactttcg    360 aaagaccccca acgagaagcg cgatcacatg gtcctgctgg agttcgtgac cgccgccggg    420
atcactctcg gcatggacga gctgtacaag gcggtaccg gagggagcat ggtgagcaag    480
ggcgaggagc tgttcaccgg ggtggtgccc atcctggtcg agctggacgg cgacgtaaac    540
ggccacaagt tcagcgtgtc cggcgagggt gagggcgatg ccacctacgg caagctgacc    600
ctgaagttca tctgcaccac cggcaagctg cccgtgccct ggcccaccct cgtgaccacc    660
ctgacctacg gcgtgcagtg cttcagccgc taccccgacc acatgaagca gcacgacttc    720
ttcaagtccg ccatgcccga aggctacatc caggagcgca ccatcttctt caaggacgac    780
ggcaactaca agacccgcgc cgaggtgaag ttcgagggcg acaccctggt gaaccgcatc    840
gagctgaagg gcatcgactt caaggaggac ggcaacatcc tggggcacaa gctggagtac    900
aacctgccgg accaactgac tgaagagcag atcgcagaat ttaaagaggc tttctcccta    960
tttgacaagg acggggatgg gacaataaca accaaggagc tggggacggt gatgcggtct   1020
ctggggcaga accccacaga agcagagctg caggacatga tcaatgaagt agatgccgac   1080
ggtgacggca atcgactt ccctgagttc ctgacaatga tggcaagaaa aatgaaatac     1140
acagacagtg aagaagaaat tagagaagcg ttccgtgtgt ttgataagga tggcaatggc   1200
tacatcagtg cagcagagct tcgccacgtg atgacaaacc ttggagagaa gttaacagat   1260
gaagaggttg atgaaatgat cagggaagca gacatcgatg gggatggtca ggtaaactac   1320
gaagagtttg tacaaatgat gacagcgaag tga                                 1353

<210> SEQ ID NO 4
<211> LENGTH: 450
<212> TYPE: PRT
<213> ORGANISM: Artificial Sequence
<220> FEATURE:
<223> OTHER INFORMATION: Circularly Permutated Protein
```

<400> SEQUENCE: 4

```
Met Gly Ser His His His His His Gly Met Ala Ser Met Thr Gly
 1               5                  10                  15

Gly Gln Gln Met Gly Arg Asp Leu Tyr Asp Asp Asp Lys Asp Leu
                20                  25                  30

Ala Thr Met Val Asp Ser Ser Arg Lys Trp Asn Lys Thr Gly His
            35                  40                  45

Ala Val Arg Ala Ile Gly Arg Leu Ser Ser Leu Glu Asn Val Tyr Ile
 50                  55                  60

Lys Ala Asp Lys Gln Lys Asn Gly Ile Lys Ala Asn Phe Lys Ile Arg
 65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
                100                 105                 110

Leu Ser Val Gln Ser Lys Leu Ser Lys Asp Pro Asn Glu Lys Arg Asp
            115                 120                 125

His Met Val Leu Leu Glu Phe Val Thr Ala Ala Gly Ile Thr Leu Gly
 130                 135                 140

Met Asp Glu Leu Tyr Lys Gly Gly Thr Gly Gly Ser Met Val Ser Lys
 145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
                180                 185                 190

Asp Ala Thr Tyr Gly Lys Leu Thr Leu Lys Phe Ile Cys Thr Thr Gly
            195                 200                 205

Lys Leu Pro Val Pro Trp Pro Thr Leu Val Thr Thr Leu Thr Tyr Gly
 210                 215                 220

Val Gln Cys Phe Ser Arg Tyr Pro Asp His Met Lys Gln His Asp Phe
 225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
            275                 280                 285

Glu Asp Gly Asn Ile Leu Gly His Lys Leu Glu Tyr Asn Leu Pro Asp
 290                 295                 300

Gln Leu Thr Glu Glu Gln Ile Ala Glu Phe Lys Glu Ala Phe Ser Leu
 305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asp Gly Thr Ile Asp Phe Pro
            355                 360                 365

Glu Phe Leu Thr Met Met Ala Arg Lys Met Lys Tyr Thr Asp Ser Glu
            370                 375                 380

Glu Glu Ile Arg Glu Ala Phe Arg Val Phe Asp Lys Asp Gly Asn Gly
 385                 390                 395                 400

Tyr Ile Ser Ala Ala Glu Leu Arg His Val Met Thr Asn Leu Gly Glu
```

```
                    405                 410                 415
Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
        435                 440                 445

Ala Lys
    450

<210> SEQ ID NO 5
<211> LENGTH: 1353
<212> TYPE: DNA
<213> ORGANISM: Artificial Sequence
<220> FEATURE:
<223> OTHER INFORMATION: Circularly Permutated DNA

<400> SEQUENCE: 5
atgggttctc atcatcatca tcatcatggt atggctagca tgactggtgg acagcaaatg      60
ggtcgggatc tgtacgacga tgacgataag gatctcgcca ccatggtcga ctcatcacgt     120
cgtaagtgga ataagacagg tcacgcagtc agagctatag gtcggctgag ctcactcgag     180
aacgtctata tcaaggccga caagcagaag aacggcatca aggcgaactt caagatccgc     240
cacaacatcg aggacggcgg cgtgcagctc gcctaccact accagcagaa cacccccatc     300
ggcgacggcc ccgtgctgct gcccgacaac cactacctga gcgtgcagtc caaactttcg     360
aaagacccca cgagaagcg cgatcacatg gtcctgctgg agttcgtgac cgccgccggg     420
atcactctcg gcatggacga gctgtacaag gcggtaccg agggagcat ggtgagcaag      480 ggcgaggagc tgttcaccgg ggtggtgccc atcctggtcg agctggacgg cgacgtaaac     540
ggccacaagt tcagcgtgtc cggcgagggt gagggcgatg ccacctacgg caagctgacc     600
ctgaagttca tctgcaccac cggcaagctg cccgtgccct ggcccaccct cgtgaccacc     660
ctgacctacg gcgtgcagtg cttcagccgc taccccgacc acatgaagca gcacgacttc     720
ttcaagtccg ccatgcccga aggctacatc caggagcgca ccatcttctt caaggacgac     780
ggcaactaca agacccgcgc cgaggtgaag ttcgagggcg acaccctggt gaaccgcatc     840
gagctgaagg gcatcgactt caaggaggac ggcaacatcc tggggcacaa gctggagtac     900
aacctgccgg accaactgac tgaagagcag atcgcagaat ttaaagaggc tttctcccta     960
tttgacaagg acggggatgg gacaataaca accaaggagc tggggacggt gatgcggtct    1020
ctggggcaga accccacaga agcagagctg caggacatga tcaatgaagt agatgccgac    1080
ggtgacggca caatcgactt ccctgagttc ctgacaatga tggcaagaaa agggagctac    1140
agggacacgg aagaagaaat tagagaagcg ttcggtgtgt ttgataagga tggcaatggc    1200
tacatcagtg cagcagagct tcgccacgtg atgacaaacc ttggagagaa gttaacagat    1260
gaagaggttg atgaaatgat cagggaagca gacatcgatg gggatggtca ggtaaactac    1320
gaagagtttg tacaaatgat gacagcgaag tga                                 1353

<210> SEQ ID NO 6
<211> LENGTH: 450
<212> TYPE: PRT
<213> ORGANISM: Artificial Sequence
<220> FEATURE:
<223> OTHER INFORMATION: Circularly Permutated protein

<400> SEQUENCE: 6

Met Gly Ser His His His His His His Gly Met Ala Ser Met Thr Gly
1               5                   10                  15
```

-continued

```
Gly Gln Gln Met Gly Arg Asp Leu Tyr Asp Asp Asp Lys Asp Leu
                 20                  25                  30
Ala Thr Met Val Asp Ser Ser Arg Lys Trp Asn Lys Thr Gly His
             35                  40                  45
Ala Val Arg Ala Ile Gly Arg Leu Ser Ser Leu Glu Asn Val Tyr Ile
 50                  55                  60
Lys Ala Asp Lys Gln Lys Asn Gly Ile Lys Ala Asn Phe Lys Ile Arg
 65                  70                  75                  80
His Asn Ile Glu Asp Gly Gly Val Gln Leu Ala Tyr His Tyr Gln Gln
                 85                  90                  95
Asn Thr Pro Ile Gly Asp Gly Pro Val Leu Leu Pro Asp Asn His Tyr
             100                 105                 110
Leu Ser Val Gln Ser Lys Leu Ser Lys Asp Pro Asn Glu Lys Arg Asp
             115                 120                 125
His Met Val Leu Leu Glu Phe Val Thr Ala Ala Gly Ile Thr Leu Gly
 130                 135                 140
Met Asp Glu Leu Tyr Lys Gly Gly Thr Gly Gly Ser Met Val Ser Lys
 145                 150                 155                 160
Gly Glu Glu Leu Phe Thr Gly Val Val Pro Ile Leu Val Glu Leu Asp
                 165                 170                 175
Gly Asp Val Asn Gly His Lys Phe Ser Val Ser Gly Glu Gly Glu Gly
             180                 185                 190
Asp Ala Thr Tyr Gly Lys Leu Thr Leu Lys Phe Ile Cys Thr Thr Gly
             195                 200                 205
Lys Leu Pro Val Pro Trp Pro Thr Leu Val Thr Thr Leu Thr Tyr Gly
 210                 215                 220
Val Gln Cys Phe Ser Arg Tyr Pro Asp His Met Lys Gln His Asp Phe
 225                 230                 235                 240
Phe Lys Ser Ala Met Pro Glu Gly Tyr Ile Gln Glu Arg Thr Ile Phe
                 245                 250                 255
Phe Lys Asp Asp Gly Asn Tyr Lys Thr Arg Ala Glu Val Lys Phe Glu
             260                 265                 270
Gly Asp Thr Leu Val Asn Arg Ile Glu Leu Lys Gly Ile Asp Phe Lys
             275                 280                 285
Glu Asp Gly Asn Ile Leu Gly His Lys Leu Glu Tyr Asn Leu Pro Asp
 290                 295                 300
Gln Leu Thr Glu Glu Gln Ile Ala Glu Phe Lys Glu Ala Phe Ser Leu
 305                 310                 315                 320
Phe Asp Lys Asp Gly Asp Gly Thr Ile Thr Thr Lys Glu Leu Gly Thr
                 325                 330                 335
Val Met Arg Ser Leu Gly Gln Asn Pro Thr Glu Ala Glu Leu Gln Asp
             340                 345                 350
Met Ile Asn Glu Val Asp Ala Asp Gly Asp Gly Thr Ile Asp Phe Pro
             355                 360                 365
Glu Phe Leu Thr Met Met Ala Arg Lys Gly Ser Tyr Arg Asp Thr Glu
 370                 375                 380
Glu Glu Ile Arg Glu Ala Phe Gly Val Phe Asp Lys Asp Gly Asn Gly
 385                 390                 395                 400
Tyr Ile Ser Ala Ala Glu Leu Arg His Val Met Thr Asn Leu Gly Glu
                 405                 410                 415
Lys Leu Thr Asp Glu Glu Val Asp Glu Met Ile Arg Glu Ala Asp Ile
             420                 425                 430
```

Asp Gly Asp Gly Gln Val Asn Tyr Glu Glu Phe Val Gln Met Met Thr
          435                 440                 445

Ala Lys
    450

<210> SEQ ID NO 7
<211> LENGTH: 1353
<212> TYPE: DNA
<213> ORGANISM: Artificial Sequence
<220> FEATURE:
<223> OTHER INFORMATION: Circularly Permutated DNA

<400> SEQUENCE: 7

| | | |
|---|---|---:|
| atgggttctc atcatcatca tcatcatggt atggctagca tgactggtgg acagcaaatg | | 60 |
| ggtcgggatc tgtacgacga tgacgataag gatctcgcca ccatggtcga ctcatcacgt | | 120 |
| cgtaagtgga ataagacagg tcacgcagtc agagctatag gtcggctgag ctcactcgag | | 180 |
| aacgtctata tcaaggccga caagcagaag aacggcatca aggcgaactt ccacatccgc | | 240 |
| cacaacatcg aggacggcgg cgtgcagctc gcctaccact accagcagaa caccccccatc | | 300 |
| ggcgacggcc ccgtgctgct gcccgacaac cactacctga gcgtgcagtc caaactttcg | | 360 |
| aaagacccca cgagaagcg cgatcacatg gtcctgctgg agttcgtgac cgccgccggg | | 420 |
| atcactctcg gcatggacga gctgtacaag ggcggtaccg gagggagcat ggtgagcaag | | 480 |
| ggcgaggagc tgttcaccgg ggtggtgccc atcctggtcg agctggacgg cgacgtaaac | | 540 |
| ggccacaagt tcagcgtgtc cggcgagggt gagggcgatg ccacctacgg caagctgacc | | 600 |
| ctgaagttca tctgcaccac cggcaagctg cccgtgccct ggcccaccct cgtgaccacc | | 660 |
| ctgacctacg gcgtgcagtg cttcagccgc taccccgacc acatgaagca gcacgacttc | | 720 |
| ttcaagtccg ccatgcccga aggctacatc caggagcgca ccatcttctt caaggacgac | | 780 |
| ggcaactaca agacccgcgc cgaggtgaag ttcgagggcg acaccctggt gaaccgcatc | | 840 |
| gagctgaagg gcatcgactt caaggaggac ggcaacatcc tggggcacaa gctggagtac | | 900 |
| aacctgccgg accaactgac tgaagagcag atcgcagaat ttaaagaggc tttctcccta | | 960 |
| tttgacaagg acggggatgg gacaataaca accaaggagc tggggacggt gatgcggtct | | 1020 |
| ctggggcaga accccacaga agcagagctg caggacatga tcaatgaagt agatgccgac | | 1080 |
| ggtgacggca caatcgactt ccctgagttc ctgacaatga tggcaagaaa aatgaaatac | | 1140 |
| agggacacgg aagaagaaat tagagaagcg ttcggtgtgt ttgataagga tggcaatggc | | 1200 |
| tacatcagtg cagcagagct tcgccacgta atgacaaacc ttggagagaa gttaacagat | | 1260 |
| gaagaggttg atgaaatgat cagggaagca gacatcgatg gggatggtca ggtaaactac | | 1320 |
| gaagagtttg tacaaatgat gacagcgaag tga | | 1353 |

<210> SEQ ID NO 8
<211> LENGTH: 450
<212> TYPE: PRT
<213> ORGANISM: Artificial Sequence
<220> FEATURE:
<223> OTHER INFORMATION: Circularly Permutated protein

<400> SEQUENCE: 8

Met Gly Ser His His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His

```
                35                  40                  45
Ala Val Arg Ala Ile Gly Arg Leu Ser Ser Leu Glu Asn Val Tyr Ile
 50                  55                  60
Lys Ala Asp Lys Gln Lys Asn Gly Ile Lys Ala Asn Phe His Ile Arg
 65                  70                  75                  80
His Asn Ile Glu Asp Gly Gly Val Gln Leu Ala Tyr His Tyr Gln Gln
                     85                  90                  95
Asn Thr Pro Ile Gly Asp Gly Pro Val Leu Leu Pro Asp Asn His Tyr
                100                 105                 110
Leu Ser Val Gln Ser Lys Leu Ser Lys Asp Pro Asn Glu Lys Arg Asp
                115                 120                 125
His Met Val Leu Leu Glu Phe Val Thr Ala Ala Gly Ile Thr Leu Gly
                130                 135                 140
Met Asp Glu Leu Tyr Lys Gly Gly Thr Gly Gly Ser Met Val Ser Lys
145                 150                 155                 160
Gly Glu Glu Leu Phe Thr Gly Val Val Pro Ile Leu Val Glu Leu Asp
                165                 170                 175
Gly Asp Val Asn Gly His Lys Phe Ser Val Ser Gly Glu Gly Glu Gly
                180                 185                 190
Asp Ala Thr Tyr Gly Lys Leu Thr Leu Lys Phe Ile Cys Thr Thr Gly
                195                 200                 205
Lys Leu Pro Val Pro Trp Pro Thr Leu Val Thr Thr Leu Thr Tyr Gly
210                 215                 220
Val Gln Cys Phe Ser Arg Tyr Pro Asp His Met Lys Gln His Asp Phe
225                 230                 235                 240
Phe Lys Ser Ala Met Pro Glu Gly Tyr Ile Gln Glu Arg Thr Ile Phe
                245                 250                 255
Phe Lys Asp Asp Gly Asn Tyr Lys Thr Arg Ala Glu Val Lys Phe Glu
                260                 265                 270
Gly Asp Thr Leu Val Asn Arg Ile Glu Leu Lys Gly Ile Asp Phe Lys
                275                 280                 285
Glu Asp Gly Asn Ile Leu Gly His Lys Leu Glu Tyr Asn Leu Pro Asp
                290                 295                 300
Gln Leu Thr Glu Glu Gln Ile Ala Glu Phe Lys Glu Ala Phe Ser Leu
305                 310                 315                 320
Phe Asp Lys Asp Gly Asp Gly Thr Ile Thr Thr Lys Glu Leu Gly Thr
                325                 330                 335
Val Met Arg Ser Leu Gly Gln Asn Pro Thr Glu Ala Glu Leu Gln Asp
                340                 345                 350
Met Ile Asn Glu Val Asp Ala Asp Gly Asp Gly Thr Ile Asp Phe Pro
                355                 360                 365
Glu Phe Leu Thr Met Met Ala Arg Lys Met Lys Tyr Arg Asp Thr Glu
                370                 375                 380
Glu Glu Ile Arg Glu Ala Phe Gly Val Phe Asp Lys Asp Gly Asn Gly
385                 390                 395                 400
Tyr Ile Ser Ala Ala Glu Leu Arg His Val Met Thr Asn Leu Gly Glu
                405                 410                 415
Lys Leu Thr Asp Glu Glu Val Asp Glu Met Ile Arg Glu Ala Asp Ile
                420                 425                 430
Asp Gly Asp Gly Gln Val Asn Tyr Glu Glu Phe Val Gln Met Met Thr
                435                 440                 445
Ala Lys
450
```

<210> SEQ ID NO 9
<211> LENGTH: 1353
<212> TYPE: DNA
<213> ORGANISM: Artificial Sequence
<220> FEATURE:
<223> OTHER INFORMATION: Circularly Permutated DNA

<400> SEQUENCE: 9

```
atgggttctc atcatcatca tcatcatggt atggctagca tgactggtgg acagcaaatg      60
ggtcgggatc tgtacgacga tgacgataag gatctcgcca ccatggtcga ctcatcacgt     120
cgtaagtgga ataagacagg tcacgcagtc agagctatag gtcggctgag ctcactcgag     180
aacgtctata tcaaggccga caagcagaag aacggcatca aggcgaactt caagatccgc     240
cacaacatcg aggacggcgg cgtgcagctc gcctaccact accagcagaa cacccccatc     300
ggcgacggcc ccgtgctgct gcccgacaac cactacctga gcgtgcagtc caaactttcg     360
aaagacccca cgagaagcg cgatcacatg gtcctgctgg agttcgtgac cgccgccggg     420
atcactctcg gcatggacga gctgtacaag ggcggtaccg agggagcat ggtgagcaag     480
ggcgaggagc tgttcaccgg ggtggtgccc atcctggtcg agctggacgg cgacgtaaac     540
ggccacaagt tcagcgtgtc cggcgagggt gagggcgatg ccacctacgg caagctgacc     600
ctgaagttca tctgcaccac cggcaagctg cccgtgccct ggcccaccct cgtgaccacc     660
ctgacctacg gcgtgcagtg cttcagccgc taccccgacc acatgaagca gcacgacttc     720
ttcaagtccg ccatgcccga aggctacatc caggagcgca ccatcttctt caaggacgac     780
ggcaactaca agacccgcgc cgaggtgaag ttcgagggcg acaccctggt gaaccgcatc     840
gagctgaagg gcatcgactt caaggaggac ggcaacatcc tggggcacaa gctggagtac     900
aacctgccgg accaactgac tgaagagcag atcgcagaat ttaaagagga attctcccta     960
tttgacaagg acggggatgg gacaataaca accaaggagc tggggacggt gatgcggtct    1020
ctggggcaga accccacaga agcagagctg caggacatga tcaatgaagt agatgccgac    1080
ggtgacggca aatcgacttc ccctgagttc ctgacaatga tggcaagaaa aatgaaatac    1140
agggacacgg aagaagaaat tagagaagcg ttcggtgtgt ttgataagga tggcaatggc    1200
tacatcagtg cagcagagct tcgccacgtg atgacaaacc ttggagagaa gttaacagat    1260
gaagaggttg atgaaatgat cagggaagca gacatcgatg gggatggtca ggtaaactac    1320
gaagagtttg tacaaatgat gacagcgaag tga                                 1353
```

<210> SEQ ID NO 10
<211> LENGTH: 450
<212> TYPE: PRT
<213> ORGANISM: Artificial Sequence
<220> FEATURE:
<223> OTHER INFORMATION: Circularly Permutated protein

<400> SEQUENCE: 10

```
Met Gly Ser His His His His His His Gly Met Ala Ser Met Thr Gly
1               5                   10                  15

Gly Gln Gln Met Gly Arg Asp Leu Tyr Asp Asp Asp Asp Lys Asp Leu
            20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
    50                  55                  60
```

```
Lys Ala Asp Lys Gln Lys Asn Gly Ile Lys Ala Asn Phe Lys Ile Arg
 65                  70                  75                  80

His Asn Ile Glu Asp Gly Gly Val Gln Leu Ala Tyr His Tyr Gln Gln
                 85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
                115                 120                 125

His Met Val Leu Leu Glu Phe Val Thr Ala Ala Gly Ile Thr Leu Gly
            130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
                180                 185                 190

Asp Ala Thr Tyr Gly Lys Leu Thr Leu Lys Phe Ile Cys Thr Thr Gly
            195                 200                 205

Lys Leu Pro Val Pro Trp Pro Thr Leu Val Thr Thr Leu Thr Tyr Gly
210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
            275                 280                 285

Glu Asp Gly Asn Ile Leu Gly His Lys Leu Glu Tyr Asn Leu Pro Asp
290                 295                 300

Gln Leu Thr Glu Glu Gln Ile Ala Glu Phe Lys Glu Gln Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asp Gly Thr Ile Asp Phe Pro
            355                 360                 365

Glu Phe Leu Thr Met Met Ala Arg Lys Met Lys Tyr Arg Asp Thr Glu
            370                 375                 380

Glu Glu Ile Arg Glu Ala Phe Gly Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
            435                 440                 445

Ala Lys
450
```

GREEN-TO-RED PHOTO-CONVERTIBLE FLUORESCENT CALCIUM INDICATOR

CROSS-REFERENCE TO RELATED APPLICATIONS

This application claims priority to provisional patent application No. 61/939,373 filed Feb. 13, 2014, the disclosure of which is hereby incorporated by reference.

FIELD OF THE DISCLOSURE

This disclosure relates to calcium indicator molecules whose fluorescence is capable of undergoing photo-conversion upon exposure to specific stimulus.

BACKGROUND OF THE DISCLOSURE

Intracellular calcium concentration is an important predictor of numerous cellular activities, which include neuronal activation, muscle cell contraction and second messenger signaling. A sensitive and convenient technique to monitor the intracellular calcium levels is through the genetically encoded calcium indicator (GECI). Among the GECIs, green fluorescent protein (GFP) based calcium sensors named GCaMPs are the most efficient and widely used tool. GCaMPs have a backbone of circularly permutated GFP protein (Baird et al, Proc. Natl. Acad. Sci. USA Vol. 96, pp. 11241-11246, 1999) fused with a chicken myosin light chain (M13) at N-terminus and a calmodulin (CaM) at C-terminus Some GCaMPs yield distinct fluorescence emission spectra (Zhao et al, 30 September Vol. 333, 2011).

SUMMARY OF THE DISCLOSURE

We have identified and developed a new category of GCaMPs (circularly permutated molecules of GFP fused with M13 and Calmodulin) that shift fluorescence emission spectra upon light exposure while maintaining calcium responsiveness. This invention has broad applications in the studies of biological sciences.

The GCaMPs of the present disclosure change from green to red fluorescence upon exposure to blue light. In one embodiment, this change is irreversible. Our green-to-red photo-convertible GCaMPs allow the use of blue light to label cells with spatial and temporal precision, thereby remedying the lack of discrete expression often conferred by broadly expressed drivers. A cell of interest can be labeled by red fluorescence converted from green fluorescence upon the blue light exposure. The labeled cells can be easily distinguished from its neighboring GCaMP-expressing cells. The GCaMPs of the present disclosure undergo an irreversible fluorescence shift from green to red fluorescence, which serves as the second fluorescent moiety in double labeling experiment. The converted red-GCaMP continues to be calcium responsive. In one embodiment, based on the present disclosure, a subpopulation of migratory or circulating cells, or different subcellular compartments can be labeled by using blue light and their intracellular calcium levels can be monitored.

BRIEF DESCRIPTION OF THE FIGURES

The patent or application file contains at least one drawing executed in color. Copies of this patent or patent application publication with color drawing(s) will be provided by the Office upon request and payment of the necessary fee.

(FIGS. 1A-1B) Fluorescent micrographs of dissected brains of *Drosophila melanogaster* expressing UAS-GCaMP3.0; IR8a-GAL4 (FIG. 1A) or UAS-GCaMP6m; NP225-Gal4 (FIG. 1B). The dissected brains were exposed to blue light (mercury arc light passed through a Zeiss 63× oil-immerse objective) for different durations as indicated on the top of each panel. Green (top) and red (bottom) fluorescence micrographs were captured using a confocal microscope. Scale bar: 20 uM. (FIG. 1C) Green-to-red photoconversion of GCaMP3.0 as quantified by the ratio of red-to-green fluorescence intensity (y-axis) by the exposure to Xenon lamp at a wavelength of 450-500 nm (x-axis).

FIGS. 2A-2C. Converted red-fluorescent GCaMP3.0 remains calcium sensitive. (FIG. 2A) Calcium imaging of a dissected fly brain expressing UAS-GCaMP3.0 by IR8a-GAL4 driver in response to depolarizing reagent, potassium chloride (40 mM KCl). Images of red fluorescence from a brain tissue before (top panel) and after (bottom panel, pseudo-colored) KCl stimulation were shown. Scale bar: 10 um. (FIG. 2B) Quantification of changes in GCaMP3.0 fluorescent intensity ($\mu$F/F) and GCaMP6.0 (FIG. 2C) in response to KCl depolarization.

FIGS. 3A-3C. The amino acid residues that are critical for green-to-red photo-conversion. (FIG. 3A) A 3-D crystal structure of the GCaMP3.0 protein showing GFP backbone in green, calmodulin in brown and myosin M13 in blue. The spatial positions of amino acid Ile79 and Val115 were highlighted in purple. (FIGS. 3B-3C) Control and mutant GCaMP3.0s were expressed in HEK293 cells. Green (top row), red (middle row) and merged (bottom row) fluorescent micrographs were taken before and after the cells were exposed to blue light (mercury arc light passed through a Zeiss 40× oil-immerse objective) for either 5 min (FIG. 3B) or 2 min (FIG. 3C). Note that V115T mutation led to a loss of green to red photo-conversion, and I79T mutation improved the efficiency of green to red photo-conversion. Scale bar: 20 μm.

(FIG. 8A) Different GCaMP variants were expressed in HEK293 cells. Green (top row), red (middle row) and merged (bottom row) fluorescent micrographs were taken after the cells were exposed to blue light (mercury arc light passed through a FITC and a Zeiss 63× oil-immerse objective) for 5 minutes. (FIG. 8B) A fly brain carrying IR64a-Gal4 and UAS-GCaMP1.6 transgene was exposed to blue light for different amount of time as indicated. Green (top row) and red (bottom row) fluorescent confocal micrographs were taken. Note that GCaMP1.6 does not undergo green-to-red photo-conversion. Instead, green fluorescence is bleached upon light exposure.

DETAILED DESCRIPTION OF THE DISCLOSURE

Figure 1A:
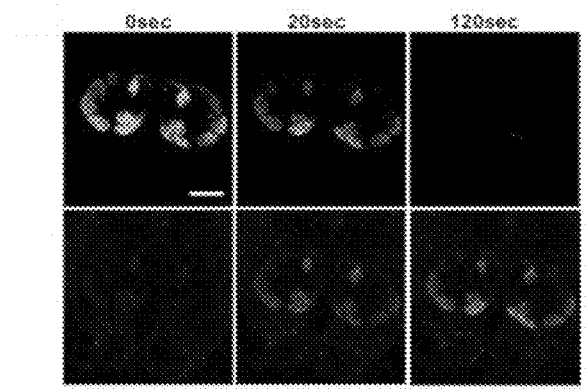
FIGS. 1A-1C. GCaMP3.0 is converted from green to red fluorescence after exposure to blue light.

Genetically encoded fluorescent calcium indicators (GECI) are useful in many areas of biomedical research. However, current GECIs have several limitations. GECI expression is controlled by drivers that often have broad expression patterns and therefore, lacks spatial and temporal resolution. GECI fluorescence in a cell of interest could be interfered by overlapping fluorescence from neighboring cells. Each GECI has a single spectrum color range. Thus, it would be valuable to introduce a second fluorescent moiety during double labeling experiment and monitor the intracellular calcium concentrations using the second fluorescence (such as red color). GECI with another emission spectra, red-GECI, has been developed, but its calcium sensitivity and fluorescence efficacy is sub-optimal. A more sensitive red calcium indicator is needed. It is currently difficult to monitor the intracellular calcium levels of a subpopulation of cells within a population of migratory or circulating cells, or to detect the intracellular calcium levels of subcellular compartments within a single cell using GECIs.

This disclosure provides compositions and methods wherein two powerful fluorescence applications, namely "highlighting" and "calcium sensing", are combined into one tool. The calcium sensing is provided by the ability of the GECI's to quantitatively detect calcium. The highlighting is provided by the ability of the same molecule to irreversibly change from green to red fluorescence thereby "marking" or "highlighting" or "labeling" a cell or a group or set of cells.

Provided in this disclosure are methods for measuring and monitoring calcium levels in cells. Also provided are compositions for detecting and monitoring calcium levels within cells. The compositions comprise nucleic acid sequences and polypeptides encoding genetically encoded calcium indicators (GECI). The GECIs of this disclosure are green-to-red photo-convertible molecules. The GECIs of the present disclosure are GCaMP molecules. Also provided are vectors and cells comprising the nucleic acids or polypeptides encoding the GCaMP molecules. Kits are also provided comprising one or more of the molecules provided herein, and instructions and/or other materials useful or necessary for carrying out the methods described herein.

The term "green-to-red fluorescence photo-conversion" is used herein to describe a phenomenon where the blue light exposure (450-500 nm wavelength and all integer values there between) of GCaMP molecules converts their green fluorescence (such as 522 nm emission) to red fluorescence (such as 600 nm emission).

In one aspect, the present disclosure provides nucleic acid sequences encoding and polypeptide sequences of GCaMP molecules which have the property of emitting green fluorescence when excited at wavelength of 488 nm. The green fluorescence is converted to red fluorescence emission after continued exposure to blue light (450-500 nm in wavelength). Thus, these molecules change fluorescence from green to red when exposed to blue light. These molecules are GFP based molecules. In one embodiment, the molecules are GCaMP molecules. The GCaMPs are formed by fusion of M13 and calmodulin protein to N- and C-termini of circularly permutated GFP. In one embodiment, the molecule is GCaMP3.0 (also referred to herein as GCaMP3. The DNA sequence for GCaMP3.0 is provided as SEQ ID NO:1. The amino acid sequence for GCaMP3 is provided as SEQ ID NO:2. In another embodiment, the GECI of the present disclosure is GCaMP5.0 (also referred to herein as GCaMP5 or GCaMP5g. The DNA sequence for GCaMP5.0 is provided as SEQ ID NO:3. The amino acid sequence for GCaMP5 is provided as SEQ ID NO:4. In another embodiment, the GECI is a GCaMP6 (also referred to as GCaMP6m or GCaMP6.0) or a variant of GCaMP6. In one embodiment, the variants are GCaMP6f and GCaMP6s. The DNA sequence for GCaMP6f is SEQ ID NO:9, for GCaMP6m is SEQ ID NO:5, and for GCaMP6s is SEQ ID NO:7. The amino acids sequence for GCaMP6f is SEQ ID NO:10, for GCaMP6m is SEQ ID NO:6, and for GCaMP6s is SEQ ID NO:8. Although DNA sequences are provided for these GCaMPs, the sequences may vary due to redundancy of the genetic code. In other embodiments, the GECI molecules are variants of the above molecules or other known GCaMPs, which display the green-to-red fluorescence shift upon exposure to blue light. As used herein the term blue light refers to a wavelength of 450-500 nm and all integer wavelengths therebetween.

In one embodiment, both the green fluorescence and the conversion to red fluorescence are observed by illuminating blue light on the cells. A source of blue light that works effectively is the mercury arc light. In one embodiment, the green and red fluorescence can be visualized by mercury arc lamp, which is available within a confocal microscope or a two-photon microscope. In one embodiment, the light is not direct laser light.

Variants of GCaMP3, GCaMP5 and GCaMP6 provided in the present disclosure include those that are at least 90% identical to GCaMP3 or GCaMP5. In various embodiments, the variants have an amino acid sequence that is 90 to 99% (and all integer values therebetween) identical to GCaMP3, GCaMP5, or GCaMP6. In one embodiment, the variants have an amino acid sequence that is at least 95% identical to the GCaMP3, GCaMP5, GCaMP6, GCaMP6s or GCaMP6f. The variants are such that they are efficiently converted from green to red fluorescence when exposed to light of one or more wavelengths of 450 to 500 nm. Based on the findings provided in this disclosure, it is well within the purview of those skilled in the art to test variants for the green to red fluorescence shift capability. In one embodiment, the variants comprise amino acid substitutions.

Variants that have specific amino acid substitutions can be made by methods well known in the art. For example, single amino acid substitutions can be made by site-directed mutagenesis whereby DNA encoding the modified protein is produced. The DNA can be expressed in recombinant cells. Such techniques are well within the purview of those skilled in the art.

In one aspect, this disclosure provides a method for screening for variants of GCaMPs for the ability of irreversibly shift from green to red fluorescence. The method comprises preparing a plurality of mutants having at least 90% to 99% identity with GCaMP or preparing variants having single amino acid substitutions, administering to cells the variants of GCaMPs (either polynucleotides or the polypeptides), checking for green fluorescence emission; continuing exposing the cells in which there is green fluorescence to blue light (450-500 nm) for a suitable period of time (such as up to 5 minutes or longer); and identifying the variants as desirable in which there is red fluorescence. In one embodiment, the cells are exposed to from at least 1 to 5 minutes and all times therebetween.

Using variants that have a single point change from the sequence of GCaMP3, it was observed that if the amino acid Valine at position 115 was replaced with amino acids threonine, alanine, glycine or tryptophan, either the green fluorescence was lost or the green to red fluorescence shift was not observed. Thus, in one embodiment, the variant of GCaMP3.0, GCaMP5.0 or GCaMP6.0 does not entail a change at the 115 position and has Valine at this position. In another embodiment, a variant of GCaMP3, GCaMP5 or GCaMP6 is provided in which the amino acid at position 79 is either Isoleucine or Threonine. In one embodiment, the amino acid at position 117 can be either Serine or Alanine. In various embodiments, the amino acid at position 79 is not Glycine, at position 222 is not Histidine and at position 225 is not Asparagine. In one embodiment, the sequence of the GCaMP is the sequence of GCaMP3.0 or GCaMP6.0, wherein the amino acid at the position 115 is Valine, at 79 is Isoleucine or Threonine, and at 117 is Serine or Alanine.

In one embodiment, the disclosure provides a polypeptide having the amino acid sequence of GCaMP3.0 or GCaMP6.0, wherein the isoleucine at position 79 is replaced by threonine. In one embodiment, the disclosure provides a polynucleotide encoding for the polypeptide having the amino acid sequence of GCaMP3.0 or GCaMP6.0, wherein the isoleucine at position 79 is replaced by threonine In one embodiment, the GECI is GCaMP5.0 and all its variants that show a green to red fluorescence shift upon exposure to blue light.

In one embodiment, the GECI is GCaMP6f, or GCaMP6m, or GCaMP6s and all variants that show a green to red fluorescence shift upon exposure to blue light.

In one embodiment, the variants do not entail a change at positions 222 and 225.

In one embodiment, red fluorescence is observed as epifluorescent emission. This is viewed conveniently by using epifluorescent microscopy.

In one aspect, the disclosure provides vectors (such as viral and non-viral vectors) comprising the nucleic acid sequences disclosed herein. The vectors comprise nucleic acids sequences of interest operably linked to expression control sequences, including promoter sequences, enhancer sequences, response elements, protein recognition sites, inducible elements, protein binding sequences, 5' and 3' untranslated regions (UTRs), transcriptional start sites, termination sequences, polyadenylation sequences, and the like.

In one aspect, the disclosure provides cells comprising the GECIs. In one embodiment, the cells have been exposed to blue light for sufficient period of time to make the cells exhibit irreversible red fluorescence. The cells may be isolated cells (such as cells in culture), bacterial cells (such as BL21 strain bacteria) or may be cells in vivo (such as neurons in the brain or any other organ or tissue). The cells may be mammalian, insect or bacterial cells. Method for introducing nucleic acid or protein sequences into cells are well known in the art and include transformation and transfection methods. For example, nucleic acids may be delivered into cells using standard transfection techniques (such as lipofectamine etc.) or standard transformation techniques used for introducing nucleic acids into competent bacterial cells. Polypeptide sequences may be delivered into cell using various electroporation or other techniques. In one embodiment, the cells may be stem cells including embryonic stem cells.

In one aspect, this disclosure provides non-human mammals, animals, insects or bacteria into whose cells have been introduced the nucleic acids or polypeptides of this disclosure such that the polypeptide will exhibit green-to-red fluorescence change. The animals may be transgenic animals.

Provided below are few illustrative examples of uses of the present disclosure.

In one embodiment, green-to-red convertible GECI nucleic acid or polypeptide is introduced into a cell or cells. This may be done in vitro or in vivo. If introduced into a group of cells, individual cells or a set of cells may be exposed to blue light (450-500 nm) such that the GECI is converted to red fluorescence. The time of exposure needed to convert from green to red fluorescence can vary. In one embodiment, it is at least 10 seconds. In another embodiment, it is at least 20 or 30 seconds (and all integers therebetween). In another embodiment, the time of exposure is from 30 seconds to 10 minutes (and all integer values in seconds between 30 seconds and 10 minutes). In one embodiment the time of exposure is 30 seconds, 1 minute, 1.5 minutes, 2 minutes, 2.5 minutes, 3 minutes, 3.5 minutes, 4 minutes, 4.5 minutes, and 5 minutes. In one embodiment, the exposure time for half conversion of green to red fluorescence for insect cells is from 20 to 40 seconds and for mammalian cells in vitro is from 1 minute to 3 minutes.

After exposure of cells to blue light such that the fluorescence is converted to red, the converted GCaMPs can be used to measure the intracellular levels of calcium by emitting stronger red fluorescence with the rise of the calcium levels. Monitoring of the red fluorescence over time can be used to provide real-time changes in calcium levels of cells.

Because the green-to-red conversion is irreversible, the marked cell can be tracked for migration purposes or lineage purposes. In one embodiment, our photo-convertible GCaMP can be used for in vivo calcium imaging of neuronal or muscular cells in real time with detailed spatial resolution. This can be achieved by labeling the cells or tissue of interest with spatially confined blue light to convert green to red fluorescence in GCaMP that is broadly expressed due to a lack of specific driver. Following the labeling, high resolution calcium imaging can be carried out, which monitors the red fluorescence without interfering fluorescence from neighboring cells. In one embodiment, this method can be used to study development of neuronal cells.

In one embodiment, the photo-convertible GCaMPs could be used to trace and monitor a specific subpopulation of migratory cells during embryonic development by labeling the cells at a specific developmental window and monitoring their intracellular calcium levels during the course of migration.

In one embodiment, the GCaMP can be used to monitor a subpopulation of proliferating and differentiating stem cells (or precursor cells). By labeling few cells of interest by blue light at different time points, the calcium dynamics of these labeled cells can be followed at different differentiation stages of the same animal.

In one embodiment, after delivery of GCaMP molecules to cells, the cells can be viewed (and the changes of calcium levels determined) by confocal microscopy or by two-photon laser. It is not expected that fluorescence will convert from green to red with confocal or two-photon microscopy. When desired, blue light (such as from a mercury lamp) can be shined on the cells to convert the fluorescence from green to red.

In one embodiment, the GCaMP can be applied for cell biologic studies. For example, a subcellular organelle of a cell that expresses GCaMP can be selectively photoconverted from green to red fluorescence by light exposure. The movement of the organelle and its intracellular calcium levels can be subsequently monitored by red GCaMP fluorescence.

In one embodiment, this disclosure provides a method of labeling desired cells out of a group of cells comprising: a) providing a GCaMP molecule or a polynucleotide encoding the GCaMP molecule to a group of cells, wherein the GCaMP molecule is capable of conversion from green to red fluorescence when exposed to light of wavelength from 450 to 500 nm for a sufficient period of time; and b) exposing a selected set of cells within the group to light of wavelength from 450 to 500 nm for sufficient time (such as at least 1 minute) to effect in the conversion of green fluorescence to red fluorescence, thereby labeling the selected cells. In one embodiment, the method further comprises the step of detecting red fluorescence from the labeled cells.

In one embodiment, this disclosure provides a method of measuring changes in calcium levels in cells of comprising: a) providing a GCaMP molecule or a polynucleotide encoding the GCaMP molecule to a group of cells, wherein the GCaMP molecule is capable of conversion from green to red fluorescence when exposed to light of wavelength from 450 to 500 nm for a sufficient period of time; and b) exposing a selected set of cells within the group to light of wavelength from 450 to 500 nm for sufficient time to effect in the conversion of green fluorescence to red fluorescence, and c) measuring a change in the intensity of red fluorescence, wherein the change in the intensity of red fluorescence is an indication of the change in calcium levels in the cell.

In one embodiment, this disclosure provides a method to track the fate of a cell or set of cells during a change in a biological system such as during development (such as during embryogenesis) comprising: a) providing a GCaMP molecule or a polynucleotide encoding the GCaMP molecule to a cell or group of cells during a first stage of change or development in a biological system, wherein the GCaMP molecule is capable of conversion from green to red fluorescence when exposed to light of wavelength from 450 to 500 nm for a sufficient period of time; and b) exposing a selected cell or set of cells within the group to light of wavelength from 450 to 500 nm for sufficient time (such as at least 1 minute) to effect in the conversion of green fluorescence to red fluorescence, thereby labeling the selected cells, and detecting the labeled cell or set of cells after a period of time by detecting red fluorescence.

In one embodiment, the green-to-red photo-conversion of GCaMPs also occurs in bacterial cells BL21 (FIG. 7), which can be used to conduct high throughput screens for variants/mutants of GCaMP molecules with improved green-to-red photo-conversion efficiency. A library of nucleic acids encoding a collection of random mutations in GCaMP3.0, or GCaMP5.0, or GCaMP6f, or GCaMP6m, or GCaMP6s can be generated using standard protocol (such as error-prone PCR amplification technique etc.). Such DNA library coding random mutations in GCaMPs can be introduced into BL21 bacterial cells. The individual bacterial clones expressing different GCaMP mutants can be exposed blue light. The clones that show increased efficiency of green-to-red fluorescence shift after blue light exposure can be easily selected, and their plasmid DNA isolated and sequenced to identify the mutations in the GCaMPs that lead to increased photo-conversion efficiency. Therefore, the effective green-to-red photo-conversion of GCaMPs in bacterial cells allows high throughput screen to identify new GCaMP variants with improved properties, such as higher efficiency of green-to-red photo-conversion.

While not intending to be bound by any particular theory, it is considered that the green-to-red photo-conversion of GCaMPs likely uses a mechanism different from those employed by other green-to-red photo-convertible fluorescent proteins (FPs) such as mEosFP (Wiedenmann et al, 2004), Kaede (Ando et al, 2002), DendGFP/Dendra (Gurskaya et al, 2006; Labas et al, 2002), KirkGR (Tsutsui et al, 2005; Habuchi et al, 2008), mcavRFP (Labas et al, 2002) and rfloRFP (Labas et al, 2002). The chromophore of these photo-convertible FPs all contains a tri-peptide His-Tyr-Gly. Crystal structures of some of these FPs suggest a common mechanism for green-to-red photo-conversion: light induces a cleavage of covalent bond on the peptide backbone at His residue, resulting in extended electron $\pi$-conjugation and leading to green-to-red emission spectral shift (Mizuno et al, 2003). Unlike the naturally occurring photo-convertible FPs, GCaMPs are based on GFP backbone and contain tri-peptide Ser/Thr-Tyr-Gly as the chromophore. Thus, GCaMPs and GFP likely use a different mechanism to achieve green-to-red photo-conversion.

Figure 5:
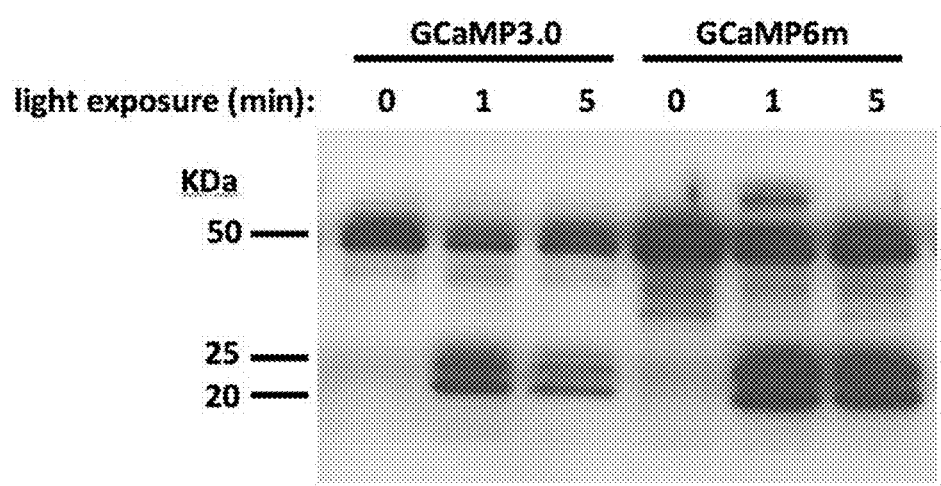
FIG. 5. GCaMPs undergo covalent bond cleavage upon blue light exposure. The brains of *Drosophila* expressing UAS-GCaMP3.0 or UAS-GCaMP6m under the control of a pan-neuronal driver nSyb-GAL4 were exposed to blue light (mercury arc light passed a 40× oil objective lens) for 0 min, 1 min or 5 min. The brain tissues were then subjected to Western blot analysis using a poly-clonal anti-GFP antibody.

Brief blue light exposure of GCaMP3.0 and GCaMP6m lead to covalent bond cleavage as visualized by Western blot analysis (FIG. 5). The cleavage event occurs in the same time frame as the green-to-red photo-conversion of GCaMPs. The precise cleavage site remains unclear.

Further, compared to other green to red convertible proteins, our photo-convertible GCaMPs offer additional utility. The photo-conversion of our GCaMPs uses light of wavelength 450 nm-500 nm as compared to ~405 nm for Keade permutated protein. Such blue light is essentially the same as light from optogenetic lasers and is harmless to most tissues even after prolonged periods of light exposure, thus making it easy and safe to apply.

The sequences of GCaMPs of the present disclosure are provided below.

```
DNA Sequence for GCaMP3.0 -
                                                SEQ ID NO: 1
ATGGGTTCTCATCATCATCATCATCATGGTATGGCTAGCATGACTGGTGGACAGCAAATG

GGTCGGGATCTGTACGACGATGACGATAAGGATCTCGCCACCATGGTCGACTCATCACGT

CGTAAGTGGAATAAGACAGGTCACGCAGTCAGAGCTATAGGTCGGCTGAGCTCACTCGA

GAACGTCTATATCAAGGCCGACAAGCAGAAGAACGGCATCAAGGCGAACTTCAAGATCC

GCCACAACATCGAGGACGGCGGCGTGCAGCTCGCCTACCACTACCAGCAGAACACCCCC

ATCGGCGACGGCCCCGTGCTGCTGCCCGACAACCACTACCTGAGCGTGCAGTCCAAACTT

TCGAAAGACCCCAACGAGAAGCGCGATCACATGGTCCTGCTGGAGTTCGTGACCGCCGC

CGGGATCACTCTCGGCATGGACGAGCTGTACAAGGGCGGTACCGGAGGGAGCATGGTGA

GCAAGGGCGAGGAGCTGTTCACCGGGGTGGTGCCCATCCTGGTCGAGCTGGACGGCGAC

GTAAACGGCCACAAGTTCAGCGTGTCCGGCGAGGGTGAGGGCGATGCCACCTACGGCAA

GCTGACCCTGAAGTTCATCTGCACCACCGGCAAGCTGCCCGTGCCCTGGCCCACCCTCGT

GACCACCCTGACCTACGGCGTGCAGTGCTTCAGCCGCTACCCCGACCACATGAAGCAGC

ACGACTTCTTCAAGTCCGCCATGCCCGAAGGCTACATCCAGGAGCGCACCATCTTCTTCA

AGGACGACGGCAACTACAAGACCCGCGCCGAGGTGAAGTTCGAGGGCGACACCCTGGTG

AACCGCATCGAGCTGAAGGGCATCGACTTCAAGGAGGACGGCAACATCCTGGGGCACAA

GCTGGAGTACAACACGCGTGACCAACTGACTGAAGAGCAGATCGCAGAATTTAAAGAGG

CTTTCTCCCTATTTGACAAGGACGGGGATGGGACAATAACAACCAAGGAGCTGGGGACG

GTGATGCGGTCTCTGGGGCAGAACCCCACAGAAGCAGAGCTGCAGGACATGATCAATGA

AGTAGATGCCGACGGTGACGGCACAATCGACTTCCCTGAGTTCCTGACAATGATGGCAA

GAAAAATGAAGACACAGACAGTGAAGAAGAAATTAGAGAAGCGTTCCGTGTGTTTGAT

AAGGATGGCAATGGCTACATCAGTGCAGCAGAGCTTCGCCACGTGATGACAAACCTTGG

AGAGAAGTTAACAGATGAAGAGGTTGATGAAATGATCAGGGAAGCAGACATCGATGGG

GATGGTCAGGTAAACTACGAAGAGTTTGTACAAATGATGACAGCGAAGTGA

Amino Acid Sequence for GCaMP3.0 -
                                                SEQ ID NO: 2
M G S H H H H H H G M A S M T G G Q Q M G R D L Y D D D D K D

L A T M V D S S R R K W N K T G H A V R A I G R L S S L E N V

Y I K A D K Q K N G I K A N F K I R H N I E D G G V Q L A Y H

Y Q Q N T P I G D G P V L L P D N H Y L S V Q S K L S K D P N

E K R D H M V L L E F V T A A G I T L G M D E L Y K G G T G G

S M V S K G E E L F T G V V P I L V E L D G D V N G H K F S V

S G E G E G D A T Y G K L T L K F I C T T G K L P V P W P T L

V T T L T Y G V Q C F S R Y P D H M K Q H D F F K S A M P E G

Y I Q E R T I F F K D D G N Y K T R A E V K F E G D T L V N R

I E L K G I D F K E D G N I L G H K L E Y N T R D Q L T E E Q

I A E F K E A F S L F D K D G D G T I T T K E L G T V M R S L

G Q N P T E A E L Q D M I N E V D A D G D G T I D F P E F L T
```

-continued

M M A R K M K D T D S E E E I R E A F R V F D K D G N G Y I S

A A E L R H V M T N L G E K L T D E E V D E M I R E A D I D G

D G Q V N Y E E F V Q M M T A K Stop

DNA Sequence for GCaMP5G -
SEQ ID NO: 3

ATGGGTTCTCATCATCATCATCATCATGGTATGGCTAGCATGACTGGTGGACAGCAAATG

GGTCGGGATCTGTACGACGATGACGATAAGGATCTCGCCACCATGGTCGACTCATCACGT

CGTAAGTGGAATAAGACAGGTCACGCAGTCAGAGCTATAGGTCGGCTGAGCTCACTCGA

GAACGTCTATATCAAGGCCGACAAGCAGAAGAACGGCATCAAGGCGAACTTCAAGATCC

GCCACAACATCGAGGACGGCGGCGTGCAGCTCGCCTACCACTACCAGCAGAACACCCCC

ATCGGCGACGGCCCCGTGCTGCTGCCCGACAACCACTACCTGAGCGTGCAGTCCAAACTT

TCGAAAGACCCCAACGAGAAGCGCGATCACATGGTCCTGCTGGAGTTCGTGACCGCCGC

CGGGATCACTCTCGGCATGGACGAGCTGTACAAGGGCGGTACCGGAGGGAGCATGGTGA

GCAAGGGCGAGGAGCTGTTCACCGGGGTGGTGCCCATCCTGGTCGAGCTGGACGGCGAC

GTAAACGGCCACAAGTTCAGCGTGTCCGGCGAGGGTGAGGGCGATGCCACCTACGGCAA

GCTGACCCTGAAGTTCATCTGCACCACCGGCAAGCTGCCCGTGCCCTGGCCCACCCTCGT

GACCACCCTGACCTACGGCGTGCAGTGCTTCAGCCGCTACCCCGACCACATGAAGCAGC

ACGACTTCTTCAAGTCCGCCATGCCCGAAGGCTACATCCAGGAGCGCACCATCTTCTTCA

AGGACGACGGCAACTACAAGACCCGCGCCGAGGTGAAGTTCGAGGGCGACACCCTGGTG

AACCGCATCGAGCTGAAGGGCATCGACTTCAAGGAGGACGGCAACATCCTGGGGCACAA

GCTGGAGTACAACCTGCCGGACCAACTGACTGAAGAGCAGATCGCAGAATTTAAAGAGG

CTTTCTCCCTATTTGACAAGGACGGGGATGGGACAATAACAACCAAGGAGCTGGGGACG

GTGATGCGGTCTCTGGGGCAGAACCCCACAGAAGCAGAGCTGCAGGACATGATCAATGA

AGTAGATGCCGACGGTGACGGCACAATCGACTTCCCTGAGTTCCTGACAATGATGGCAA

GAAAAATGAAATACACAGACAGTGAAGAAGAAATTAGAGAAGCGTTCCGTGTGTTTGAT

AAGGATGGCAATGGCTACATCAGTGCAGCAGAGCTTCGCCACGTGATGACAAACCTTGG

AGAGAAGTTAACAGATGAAGAGGTTGATGAAATGATCAGGGAAGCAGACATCGATGGG

GATGGTCAGGTAAACTACGAAGAGTTTGTACAAATGATGACAGCGAAGTGA

Amino Acid Sequence for GCaMP5g -
SEQ ID NO: 4

M G S H H H H H H G M A S M T G G Q Q M G R D L Y D D D D K D

L A T M V D S S R R K W N K T G H A V R A I G R L S S L E N V

Y I K A D K Q K N G I K A N F K I R H N I E D G G V Q L A Y H

Y Q Q N T P I G D G P V L L P D N H Y L S V Q S K L S K D P N

E K R D H M V L L E F V T A A G I T L G M D E L Y K G G T G G

S M V S K G E E L F T G V V P I L V E L D G D V N G H K F S V

S G E G E G D A T Y G K L T L K F I C T T G K L P V P W P T L

V T T L T Y G V Q C F S R Y P D H M K Q H D F F K S A M P E G

Y I Q E R T I F F K D D G N Y K T R A E V K F E G D T L V N R

I E L K G I D F K E D G N I L G H K L E Y N L P D Q L T E E Q

I A E F K E A F S L F D K D G D G T I T T K E L G T V M R S L

G Q N P T E A E L Q D M I N E V D A D G D G T I D F P E F L T

M M A R K M K Y T D S E E E I R E A F R V F D K D G N G Y I S

-continued

A A E L R H V M T N L G E K L T D E E V D E M I R E A D I D G

D G Q V N Y E E F V Q M M T A K Stop

DNA Sequence for GCaMP6m -
SEQ ID NO: 5
ATGGGTTCTCATCATCATCATCATCATGGTATGGCTAGCATGACTGGTGGACAGCAAATG

GGTCGGGATCTGTACGACGATGACGATAAGGATCTCGCCACCATGGTCGACTCATCACGT

CGTAAGTGGAATAAGACAGGTCACGCAGTCAGAGCTATAGGTCGGCTGAGCTCACTCGA

GAACGTCTATATCAAGGCCGACAAGCAGAAGAACGGCATCAAGGCGAACTTCAAGATCC

GCCACAACATCGAGGACGGCGGCGTGCAGCTCGCCTACCACTACCAGCAGAACACCCCC

ATCGGCGACGGCCCCGTGCTGCTGCCCGACAACCACTACCTGAGCGTGCAGTCCAAACTT

TCGAAAGACCCCAACGAGAAGCGCGATCACATGGTCCTGCTGGAGTTCGTGACCGCCGC

CGGGATCACTCTCGGCATGGACGAGCTGTACAAGGGCGGTACCGGAGGGAGCATGGTGA

GCAAGGGCGAGGAGCTGTTCACCGGGGTGGTGCCCATCCTGGTCGAGCTGGACGGCGAC

GTAAACGGCCACAAGTTCAGCGTGTCCGGCGAGGGTGAGGGCGATGCCACCTACGGCAA

GCTGACCCTGAAGTTCATCTGCACCACCGGCAAGCTGCCCGTGCCCTGGCCCACCCTCGT

GACCACCCTGACCTACGGCGTGCAGTGCTTCAGCCGCTACCCCGACCACATGAAGCAGC

ACGACTTCTTCAAGTCCGCCATGCCCGAAGGCTACATCCAGGAGCGCACCATCTTCTTCA

AGGACGACGGCAACTACAAGACCCGCGCCGAGGTGAAGTTCGAGGGCGACACCCTGGTG

AACCGCATCGAGCTGAAGGGCATCGACTTCAAGGAGGACGGCAACATCCTGGGGCACAA

GCTGGAGTACAACCTGCCGGACCAACTGACTGAAGAGCAGATCGCAGAATTTAAAGAGG

CTTTCTCCCTATTTGACAAGGACGGGGATGGGACAATAACAACCAAGGAGCTGGGGACG

GTGATGCGGTCTCTGGGGCAGAACCCCACAGAAGCAGAGCTGCAGGACATGATCAATGA

AGTAGATGCCGACGGTGACGGCACAATCGACTTCCCTGAGTTCCTGACAATGATGGCAA

GAAAAGGGAGCTACAGGGACACGGAAGAAGAAATTAGAGAAGCGTTCGGTGTGTTTGA

TAAGGATGGCAATGGCTACATCAGTGCAGCAGAGCTTCGCCACGTGATGACAAACCTTG

GAGAGAAGTTAACAGATGAAGAGGTTGATGAAATGATCAGGGAAGCAGACATCGATGG

GGATGGTCAGGTAAACTACGAAGAGTTTGTACAAATGATGACAGCGAAGTGA

Amino Acid Sequence for GCAMP6m -
SEQ ID NO: 6
M G S H H H H H H G M A S M T G G Q Q M G R D L Y D D D D K D

L A T M V D S S R R K W N K T G H A V R A I G R L S S L E N V

Y I K A D K Q K N G I K A N F K I R H N I E D G G V Q L A Y H

Y Q Q N T P I G D G P V L L P D N H Y L S V Q S K L S K D P N

E K R D H M V L L E F V T A A G I T L G M D E L Y K G G T G G

S M V S K G E E L F T G V V P I L V E L D G D V N G H K F S V

S G E G E G D A T Y G K L T L K F I C T T G K L P V P W P T L

V T T L T Y G V Q C F S R Y P D H M K Q H D F F K S A M P E G

Y I Q E R T I F F K D D G N Y K T R A E V K F E G D T L V N R

I E L K G I D F K E D G N I L G H K L E Y N L P D Q L T E E Q

I A E F K E A F S L F D K D G D G T I T T K E L G T V M R S L

G Q N P T E A E L Q D M I N E V D A D G D G T I D F P E F L T

M M A R K G S Y R D T E E E I R E A F G V F D K D G N G Y I S

-continued

A A E L R H V M T N L G E K L T D E E V D E M I R E A D I D G

D G Q V N Y E E F V Q M M T A K Stop

DNA SEQUENCE FOR GCAMP6s -
SEQ ID NO: 7
ATGGGTTCTCATCATCATCATCATCATGGTATGGCTAGCATGACTGGTGGACAGCAAATG

GGTCGGGATCTGTACGACGATGACGATAAGGATCTCGCCACCATGGTCGACTCATCACGT

CGTAAGTGGAATAAGACAGGTCACGCAGTCAGAGCTATAGGTCGGCTGAGCTCACTCGAG

AACGTCTATATCAAGGCCGACAAGCAGAAGAACGGCATCAAGGCGAACTTCCACATCCGC

CACAACATCGAGGACGGCGGCGTGCAGCTCGCCTACCACTACCAGCAGAACACCCCCATC

GGCGACGGCCCCGTGCTGCTGCCCGACAACCACTACCTGAGCGTGCAGTCCAAACTTTCG

AAAGACCCCAACGAGAAGCGCGATCACATGGTCCTGCTGGAGTTCGTGACCGCCGCGGG

ATCACTCTCGGCATGGACGAGCTGTACAAGGGCGGTACCGGAGGGAGCATGGTGAGCAAG

GGCGAGGAGCTGTTCACCGGGGTGGTGCCCATCCTGGTCGAGCTGGACGGCGACGTAAAC

GGCCACAAGTTCAGCGTGTCCGGCGAGGGTGAGGGCGATGCCACCTACGGCAAGCTGACC

CTGAAGTTCATCTGCACCACCGGCAAGCTGCCCGTGCCCTGGCCCACCCTCGTGACCACC

CTGACCTACGGCGTGCAGTGCTTCAGCCGCTACCCCGACCACATGAAGCAGCACGACTTC

TTCAAGTCCGCCATGCCCGAAGGCTACATCCAGGAGCGCACCATCTTCTTCAAGGACGAC

GGCAACTACAAGACCCGCGCCGAGGTGAAGTTCGAGGGCGACACCCTGGTGAACCGCATC

GAGCTGAAGGGCATCGACTTCAAGGAGGACGGCAACATCCTGGGGCACAAGCTGGAGTAC

AACCTGCCGGACCAACTGACTGAAGAGCAGATCGCAGAATTTAAAGAGGCTTTCTCCCTA

TTTGACAAGGACGGGGATGGGACAATAACAACCAAGGAGCTGGGGACGGTGATGCGGTCT

CTGGGGCAGAACCCCACAGAAGCAGAGCTGCAGGACATGATCAATGAAGTAGATGCCGAC

GGTGACGGCACAATCGACTTCCCTGAGTTCCTGACAATGATGGCAAGAAAAATGAAATAC

AGGGACACGGAAGAAGAAATTAGAGAAGCGTTCGGTGTGTTTGATAAGGATGGCAATGGC

TACATCAGTGCAGCAGAGCTTCGCCACGTGATGACAAACCTTGGAGAGAAGTTAACAGAT

GAAGAGGTTGATGAAATGATCAGGGAAGCAGACATCGATGGGGATGGTCAGGTAAACTAC

GAAGAGTTTGTACAAATGATGACAGCGAAGTGA

Amino Acid Sequence for GCAMP6s -
SEQ ID NO: 8
MGSHHHHHHG MASMTGGQQM GRDLYDDDDK DLATMVDSSR RKWNKTGHAV

RAIGRLSSLE NVYIKADKQK NGIKANFHIR HNIEDGGVQL AYHYQQNTPI

GDGPVLLPDN HYLSVQSKLS KDPNEKRDHM VLLEFVTAAG ITLGMDELYK

GGTGGSMVSK GEELFTGVVP ILVELDGDVN GHKFSVSGEG EGDATYGKLT

LKFICTTGKL PVPWPTLVTT LTYGVQCFSR YPDHMKQHDF FKSAMPEGYI

QERTIFFKDD GNYKTRAEVK FEGDTLVNRI ELKGIDFKED GNILGHKLEY

NLPDQLTEEQ IAEFKEAFSL FDKDGDGTIT TKELGTVMRS LGQNPTEAEL

QDMINEVDAD GDGTIDFPEF LTMMARKMKY RDTEEEIREA FGVFDKDGNG

YISAAELRHV MTNLGEKLTD EEVDEMIREA DIDGDGQVNY EEFVQMMTAK

DNA SEQUENCE FOR GCAMP6f -
SEQ ID NO: 9
ATGGGTTCTCATCATCATCATCATCATGGTATGGCTAGCATGACTGGTGGACAGCAAATG

GGTCGGGATCTGTACGACGATGACGATAAGGATCTCGCCACCATGGTCGACTCATCACGT

CGTAAGTGGAATAAGACAGGTCACGCAGTCAGAGCTATAGGTCGGCTGAGCTCACTCGAG

AACGTCTATATCAAGGCCGACAAGCAGAAGAACGGCATCAAGGCGAACTTCAAGATCCGC

-continued

```
CACAACATCGAGGACGGCGGCGTGCAGCTCGCCTACCACTACCAGCAGAACACCCCCATC

GGCGACGGCCCCGTGCTGCTGCCCGACAACCACTACCTGAGCGTGCAGTCCAAACTTTCG

AAAGACCCCAACGAGAAGCGCGATCACATGGTCCTGCTGGAGTTCGTGACCGCCGCCGGG

ATCACTCTCGGCATGGACGAGCTGTACAAGGGCGGTACCGGAGGGAGCATGGTGAGCAAG

GGCGAGGAGCTGTTCACCGGGGTGGTGCCCATCCTGGTCGAGCTGGACGGCGACGTAAAC

GGCCACAAGTTCAGCGTGTCCGGCGAGGGTGAGGGCGATGCCACCTACGGCAAGCTGACC

CTGAAGTTCATCTGCACCACCGGCAAGCTGCCCGTGCCCTGGCCCACCCTCGTGACCACC

CTGACCTACGGCGTGCAGTGCTTCAGCCGCTACCCCGACCACATGAAGCAGCACGACTTC

TTCAAGTCCGCCATGCCCGAAGGCTACATCCAGGAGCGCACCATCTTCTTCAAGGACGAC

GGCAACTACAAGACCCGCGCCGAGGTGAAGTTCGAGGGCGACACCCTGGTGAACCGCATC

GAGCTGAAGGGCATCGACTTCAAGGAGGACGGCAACATCCTGGGGCACAAGCTGGAGTAC

AACCTGCCGGACCAACTGACTGAAGAGCAGATCGCAGAATTTAAAGAGGAATTCTCCCTA

TTTGACAAGGACGGGGATGGGACAATAACAACCAAGGAGCTGGGGACGGTGATGCGGTCT

CTGGGGCAGAACCCCACAGAAGCAGAGCTGCAGGACATGATCAATGAAGTAGATGCCGAC

GGTGACGGCACAATCGACTTCCCTGAGTTCCTGACAATGATGGCAAGAAAAATGAAATAC

AGGGACACGGAAGAAGAAATTAGAGAAGCGTTCGGTGTGTTTGATAAGGATGGCAATGGC

TACATCAGTGCAGCAGAGCTTCGCCACGTGATGACAAACCTTGGAGAGAAGTTAACAGAT

GAAGAGGTTGATGAAATGATCAGGGAAGCAGACATCGATGGGGATGGTCAGGTAAACTAC

GAAGAGTTTGTACAAATGATGACAGCGAAGTGA
```

Amino Acid Sequence for GCAMP6f -
SEQ ID NO: 10

```
MGSHHHHHHG MASMTGGQQM GRDLYDDDDK DLATMVDSSR RKWNKTGHAV

RAIGRLSSLE NVYIKADKQK NGIKANFKIR HNIEDGGVQL AYHYQQNTPI

GDGPVLLPDN HYLSVQSKLS KDPNEKRDHM VLLEFVTAAG ITLGMDELYK

GGTGGSMVSK GEELFTGVVP ILVELDGDVN GHKFSVSGEG EGDATYGKLT

LKFICTTGKL PVPWPTLVTT LTYGVQCFSR YPDHMKQHDF FKSAMPEGYI

QERTIFFKDD GNYKTRAEVK FEGDTLVNRI ELKGIDFKED GNILGHKLEY

NLPDQLTEEQ IAEFKEEFSL FDKDGDGTIT TKELGTVMRS LGQNPTEAEL

QDMINEVDAD GDGTIDFPEF LTMMARKMKY RDTEEEIREA FGVFDKDGNG

YISAAELRHV MTNLGEKLTD EEVDEMIREA DIDGDGQVNY EEFVQMMTAK
```

The invention is further described in the following example, which is intended to be illustrative and not limiting.

EXAMPLE 1

Methods

Fly Strains

Fruit flies *Drosophila Melanogaster* were maintained on standard cornmeal food at room temperature. GCaMP transgenic flies, UAS-CD8GFP, IR8a-GAL4, NP225-GAL4 and R38H02-GAL4-GAL4 flies were generated.

DNA Constructs

GCaMP constructs based on pCMV mammalian expression vector were purchased from Addgene Inc. Point mutations were introduced using Quickchange mutagenesis (Life Technologies) following standard protocols. All constructs were sequenced to confirm the GCaMP coding sequence.

Calcium Imaging

Calcium imaging experiments were performed using a two-photon microscope as previously described (Ai et al, 2010). The dissected fly brains were pinned down on a silicone plate. A custom-built perfusion system was used to exchange the solution covering the brain. The control solution contains 108 mM NaCl, 2 mM $CaCl_2$, 8.2 mM $MgCl_2$, 4 mM $NaHCO_3$, 1 mM $NaH_2PO_4$, 5 mM Trehalose, 10 mM Sucrose, 5 mM HEPES (pH7.4). The depolarizing buffer contains an addition of 40 mM KCl. Due to the availability of reagents to the neurons inside the brain tissue, a calcium response is generally observed ~2 min after the initial exposure of the brain to the depolarizing solution.

Photo-Conversion of GCaMPs

Photo-conversion was conducted using the fly brains of 2-5 day old transgenic flies carrying IR8a-GAL4; UAS- GCaMP3.0 (in FIGS. 1A-1C and FIGS. 2A-2C). Fly brains were dissected in phosphate buffered solution (1×PBS) at room temperature. Dissected brains were mounted onto glass slides and covered with coverslip. Photo-conversion was then performed by exposing the brains to the light from a mercury lamp (HBO100 Zeiss) through a FITC filter on a Ziess microscope and a 40× or 63× oil-immerse lens. Other lens such as 10× and 20× lens can also be used to achieve photo-conversion but require longer light exposure. Green and red fluorescent micrographs were taken using a confocal microscope before and after photo-conversion. Following similar experimental procedures, photo-conversion of GCaMPs in fly brains was also achieved using a Xenon light source with adjustable wavelength (Polychrome V, Till photonics).

For photo-conversion of GCaMPs in bacterial cells, BL21 cells were transformed with pET bacterial expression vector carrying DNA sequences encoding GCaMP3.0. BL21 cells were cultured overnight at 37° C. on a kanamycin plate. To induce GCaMP expression, 0.5 ul of IPTG (0.5 mM) was added to individual clones on the plate from the overnight culture. The bacteria were incubated for an additional 4 hours at 37° C. to allow protein expression. Bacterial clones expressing GCaMP proteins were picked using a pipet tip, spread onto a glass slide, and covered by a cover-glass. Green and red fluorescent micrographs of the bacterial cells on the glass slide were taken under a confocal microscope. Then the bacterial cells were exposed to blue light from a mercury lamp passed through either a 20× air objective or a 40× oil objective for different durations. After the blue light exposure, green and red fluorescent micrographs were taken again using the same microscope with the same setting.

For photo-conversion of GCaMPs in mammalian cells, HEK293 cells were cultured on coverslip and transfected with GCaMP expressing constructs using Lipofectamine2000 reagent (Life Technologies). Two days after transfection, the coverslip containing GCaMP-expressing cells were dipped into 1×PBS for 10 seconds and then mounted onto a glass slide with the cells trapped between the glass slide and the coverslip. Photo-conversion was subsequently performed following the same procedure as photo-conversion of the fly brains.

Photo-conversion experiments for "oxidative redding" and "anaerobic redding" were performed slightly differently. HEK293 cells were cultured and transfected in glass bottom 12-well culture dish (MatTek Corporation). Two days after transfection, the photo-conversion experiments were performed. For "anaerobic redding" experiments, the culture medium was replaced with serum-free phenol-free DMEM in the presence of oxygen depleting reagents (30 ug/ml catalase, 4.5 mg/ml glucose and 250 ug/ml glucose oxidase) for 30 minutes in 37° C. incubator immediately before photo-conversion. For "oxidative redding" experiments, the culture medium was replaced with serum-free phenol-free DMEM in the presence of electron acceptor (5 mM potassium ferricyanide) for 30 minutes in 37° C. For photo-conversion, the treated cells in the 12-well dish were then exposed to blue light from an inverted Olympus microscope with 40× objective lens Western Blot A total of 10 brains from flies carrying Elav-Gal4; UAS-GCaMP3.0 were dissected in PBS. Brains were mounted onto glass slides and covered with coverslip. Photoconversion was then performed by exposing the brains to blue light on a Ziess microscope with a 63× oil-immerse lens. Each brain was exposed to blue light for 5 min Control brains were similarly dissected and mounted on glass slide but was not exposed to blue light. Brains were then homogenized with pestle and mortar in 40 ul cold PBS. Ten microliters of reducing 5×SDS-PAGE loading buffer (300 mM Tris (pH6.8), 10% SDS, 0.01% bromphenol blue, 40% glycerol and 5% beta-mercaptoethanol) was added to the homogenized tissue solution. Samples were heated to 95° C. for 5 min and subjected to SDS-PAGE electrophoresis. Rabbit anti-GFP (1:1,000, A-11122, Life Technologies), mouse anti-His (1:1,000, abcam) and HRP conjugated goat-anti-mouse secondary antibody (1:5,000, Jackson ImmunoResearch) were used to detect GCaMP3.0 proteins.

RESULTS

Green to Red Photo-Conversion of GCaMP3.0

Figure 1B:
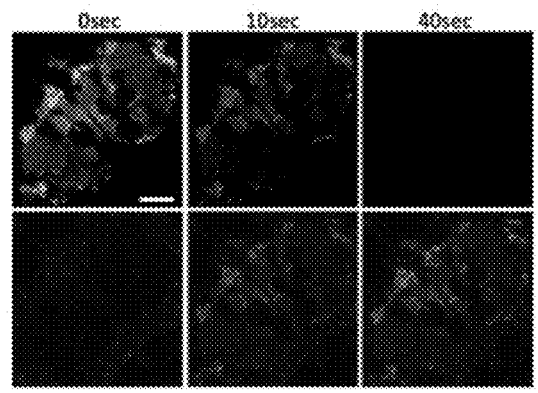
Figure 6:
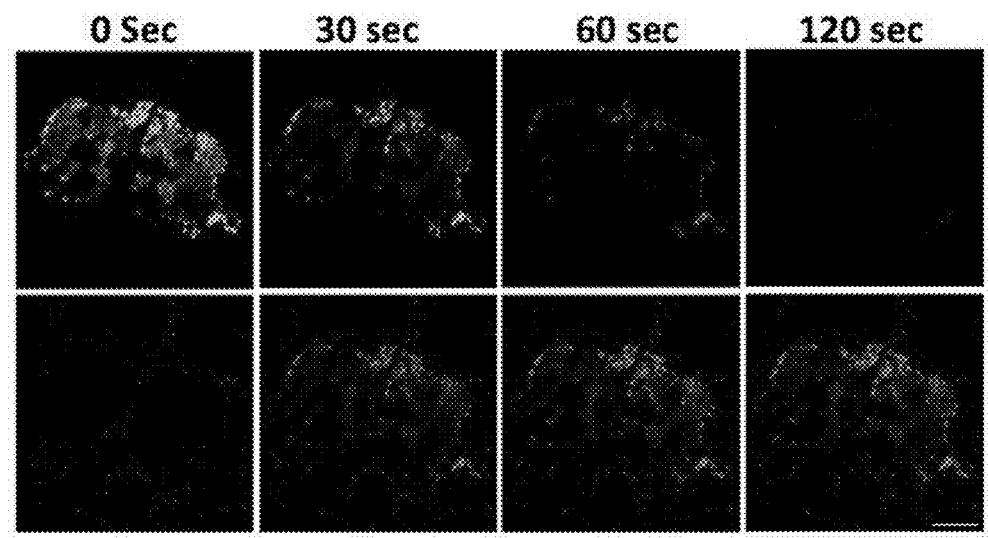
FIG. 6. GCaMP3.0 expressed in central fly neurons is converted from green to red fluorescence. Fluorescent micrographs of a pair of the antennal lobes from a dissected brain of *Drosophila melanogaster* expressing UAS-GCaMP3.0 under the control of NP225-GAL4 driver (Tanaka et al, 2008). The brain tissue was exposed to a blue light source (mercury arc light passed through a Zeiss 40× oil-immerse objective) for different durations as indicated on the top of each panel. Green (top panel) and red (bottom panel) fluorescence micrographs were captured using a confocal microscope. Scale bar: 50 nm.
Figure 8A:
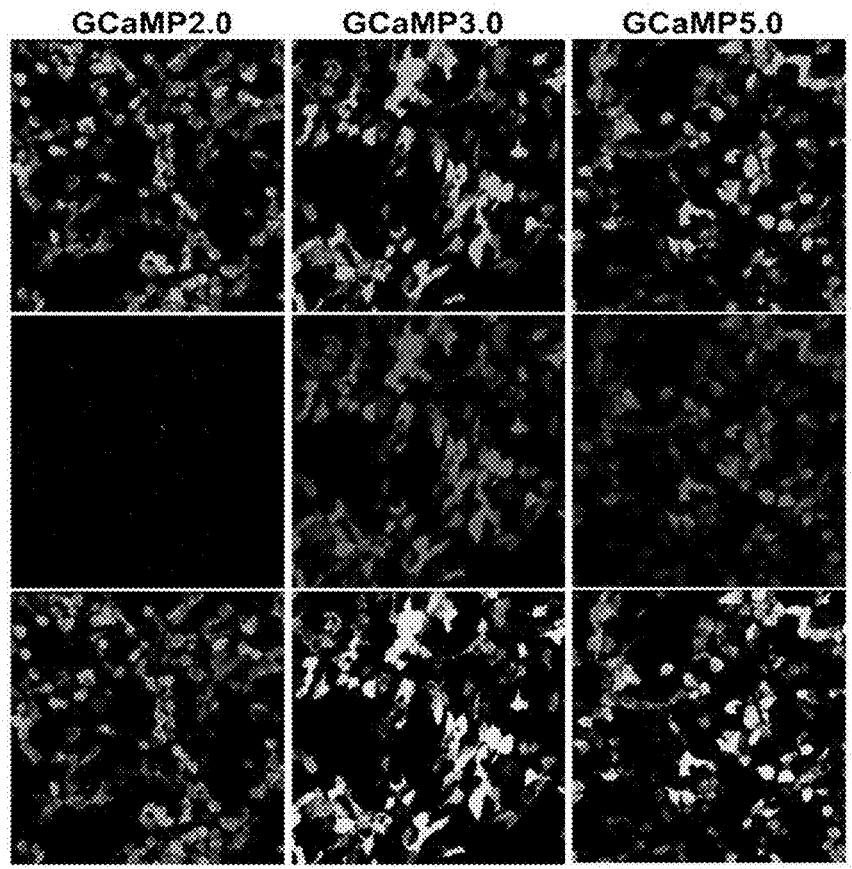
FIGS. 8A-8B. Photoconversion of GCaMP variants.

During a routine experiment with a confocal microscope, we serendipitously found that *Drosophila* olfactory sensory neurons expressing GCaMP3.0 under the control of IR8a-GAL4 (Ai et al, 2013) driver was rapidly converted from green to red fluorescence after a brief exposure to light from a mercury lamp (FIG. 1A). The fluorescence emission spectral shift can be observed after 30 seconds of the light exposure. Prolonged exposure (>2 min) to light resulted in complete loss of GCaMP3.0 green fluorescence, while the intensity of red fluorescence remained the same (FIG. 1A). The green-to-red photo-conversion of GCaMP3.0 also occurred in other fly neurons including sensory neurons and central neurons (FIG. 6). We found that GCaMP variants, GCaMP6.0 and GCaMP5.0 also undergo green-to-red photoconversion upon a brief exposure to light—as short as 10 seconds (FIG. 1B and FIG. 8A). After 40 seconds of light exposure, green fluorescence of GCaMP6.0 was completely photoconverted to red (FIG. 1B).

Figure 7:
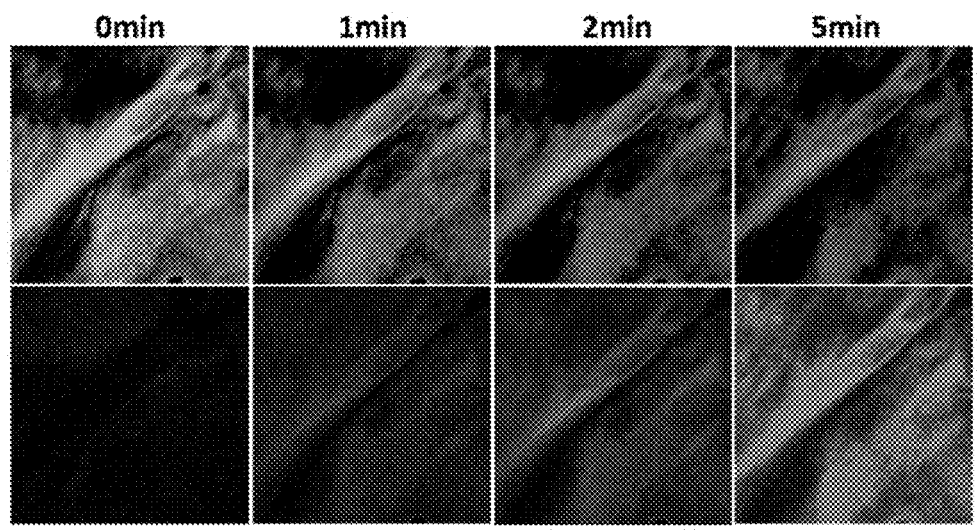
FIG. 7. Bacterial cells expressing GCaMP3.0 undergo green-to-red photo-conversion. Bacterial BL21 cells expressing GCaMP3.0 were spread onto a glass slide and covered by a coverslip. The bacterial cells were then exposed to blue light from a mercury lamp passed through a 20× objective lens for different durations as indicated in the figure.

We asked whether photo-conversion of GCaMP3.0 also occurred in other types of cells including bacterial and mammalian cells. When we expressed GCaMP3.0 in BL21 bacterial cells and exposed the cells to the blue light (see methods), we found that bacterial cells expressing GCaMP3.0 can be efficiently converted from green fluorescence (FIG. 7, top row) to red fluorescence (FIG. 7, bottom row).

Figure 8B:
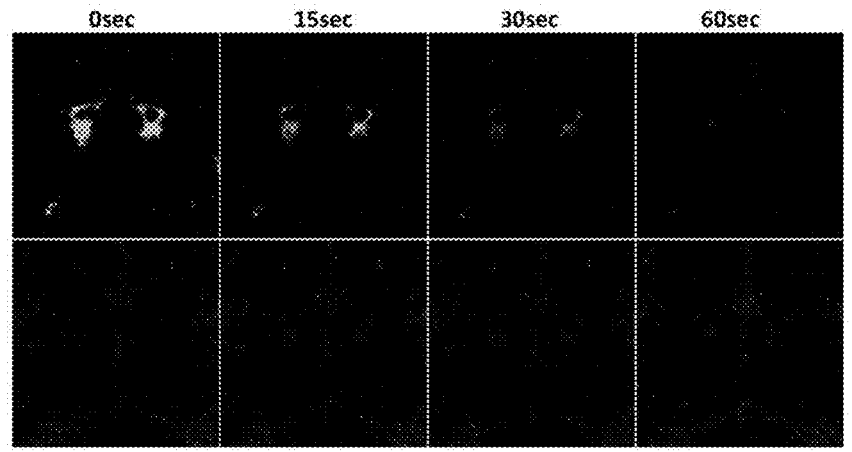

We then investigated if photoconversion also occurs in mammalian cells. We expressed GCaMP3.0 in HEK293 cells and exposed the cells to the light (see methods). We found that GCaMP3.0 also undergoes green-to-red photoconversion in HEK293 cells (FIG. 8A) and fly brains (FIG. 8B). However, the photo-conversion of GCaMP3.0 in HEK293 cells required more time than fly brains. An exposure of 2 minutes to the light was used for HEK293 cells.

Figure 1C:
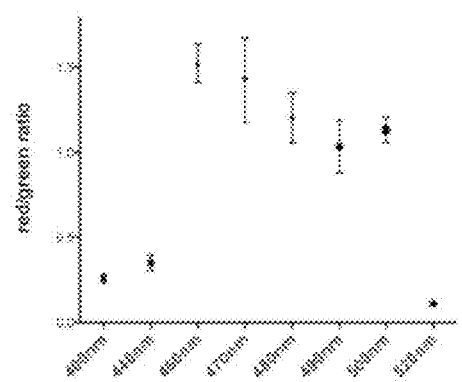

We next sought to uncover the wavelength of light that is capable of converting GCaMP3.0. We first used different filter sets to limit the wavelength of output light from a mercury lamp. We found that the light passing through DAPI, TRITC or Cy5 filter set was not capable of converting GCaMP3.0 from green to red fluorescence (data not shown). However, we found that the light passing through the FITC filter, thus blue light, is able to photo-convert GCaMP3.0. To identify the exact wavelength of light that is capable of photo-converting GCaMP3.0, we used a Xenon lamp to fine-tune the wavelength of output light. We found that the wavelength of light between 450 nm and 500 nm was able to convert green to red fluorescence (FIG. 1B FIG. 1C).

Calcium Response of the Converted Red Fluorescent GCaMP3.0

Having shown that GCaMPs undergo photoconversion, we evaluated the response of the resulting red GCaMP3.0 to determine whether photoconversion is accompanied by any change in calcium sensitivity. To this end, we carried out calcium imaging experiments in a subset of the antennal lobe expressing non-photoconverted green GCaMP3.0 and photoconverted red GCaMP3.0. Each GCaMP3.0 was exposed to potassium chloride (KCl, 40 mM), which induces depolarization and consequently, triggers the propagation of action potentials. Exposure to KCl increased the intensity of fluorescence of the converted red GCaMP3.0 by 92±19% (µF/F) compared with 217±26% for the naïve (green-fluorescent) GCaMP3.0 (FIGS. 2A and 2B). We observed similar results with further reduced sensitivity when GCaMP6.0 was expressed in a population of central neurons in the brain (FIG. 2C). Our findings indicate that GCaMPs retain calcium responsiveness when its fluorescence is converted from green to red, albeit with reduced sensitivity.

Amino Acid Residues Critical for Photo-Conversion

To identify amino acid residues in GCaMP3.0 that are required for the photo-conversion, we tested whether other variants of GCaMPs could be converted from green to red fluorescence. We found that GCaMP1.6 (Nakai et al, 2001; Wang et al, 2003) when expressed fly neurons and GCaMP2.0 (Mao et al, 2008) when expressed in HEK293 cells cannot be converted to red fluorescence after the exposure to blue light (FIGS. 8A and 8B and data not shown). By contrast, GCaMP5.0 and all variants of GCaMP6.0 can undergo this photoconversion by light exposure (FIG. 8A).

In comparison to GCaMP2.0, GCaMP3.0 has three point mutations: M66K, T116V and N363D. We note that because the Arginine in GCaMP3.0 was deleted at position 2, these three mutated amino acid residues correspond to Lys65, Val115 and Asp362 in GCaMP3.0. Of these amino acid residues, the mutation T116V occurs very close to the chromophore group in 3-dimensional space (FIG. 3A). We therefore hypothesized that the T116V mutation was the key change that rendered the conversion of the green-to-red fluorescence of GCaMP3.0. When we changed the Val115 of GCaMP3.0 back to Thr as in GCaMP2.0, we found that GCaMP3.0-V115T expressed in HEK293 cells retained green fluorescence but was not able to be converted from green to red fluorescence (FIG. 3B). Similarly, GCamp3.0-V115A could not be converted to red fluorescence (Table 1). Mutating Val115 to other amino acids such as Gly and Tyr resulted in complete loss of green fluorescence (Table 1). These results demonstrate that Val115 of GCaMP3.0 is a critical residue that is required for the conversion of green to red fluorescence in GCaMP3.0.

We next asked whether other amino acid residues, located proximal to the chromophore in space, are also required for photo-conversion. We made a series of point mutations in these amino acid residues (Table 1). Many mutations including I79G, T222H and V225N resulted in a loss of green fluorescence (Table 1), possibly due to a disruption of GFP backbone structure or an interference of the chromophore formation/maturation (Ormö et al, 1996; Yang et al, 1996). Notably, one mutation I79T resulted in increased efficiency of green-to-red photo-conversion (Table 1). For example, the maximal photo-conversion of wild-type GCaMP3.0 expressed in cultured HEK293 cells requires at least 5 minutes of the light exposure. However, GCaMP3.0-I79T can be readily converted to red fluorescence within 2 minutes of the light exposure (FIG. 3C). The increase in photo-conversion efficiency in mammalian cells will significantly enhance the application potentials of GCaMP3.0.

Figure 9:
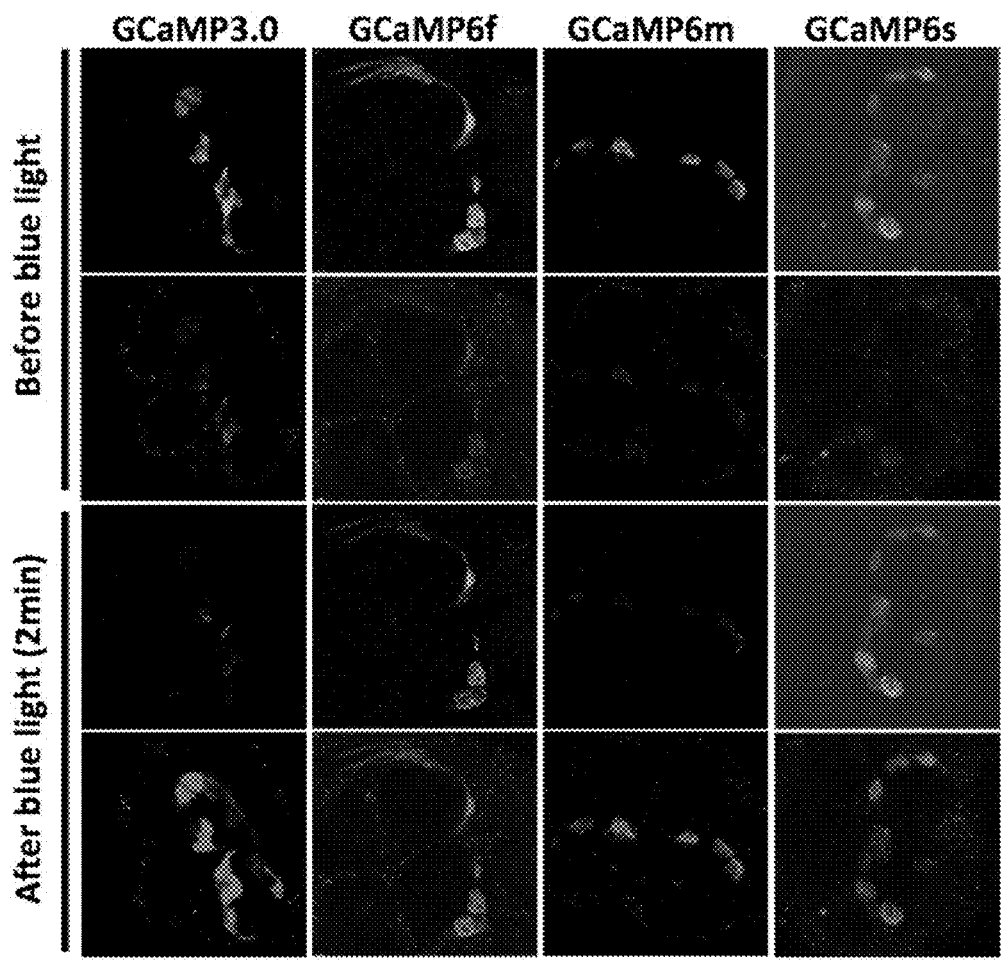
FIG. 9. GCaMP6f, GCaMP6m and GCaMP6s expressed in Drosophila brain can be photo-converted from green to red fluorescence. Fluorescent micrographs of a pair of the antennal lobes in a dissected brain of Drosophila melanogaster expressing UAS-GCaMP3.0, GCaMP6f, GCaMP6m or GCaMP6s under the control of IR8a-GAL4 driver. The brain tissue was exposed to a blue light source (mercury arc light passed through a Zeiss 40× oil-immerse objective) for 2 minutes. Green (top panel) and red (bottom panel) fluorescence micrographs were captured using a confocal microscope. Scale bar: 20 nm.

We also tested whether other versions GCaMPs, including GCaMP5G and variants of GCaMP6.0, can be converted from green to red fluorescence. We found that GCaMP5G (Akerboom et al, 2012) can be photo-converted to red fluorescence as efficient as GCaMP3.0 (FIGS. 8A-8B). Similarly, we found that GCaMP6f, GCaMP6m and GCaMP6s (Chen et al, 2013) expressed in *Drosophila* brains also undergo efficient green-to-red photo-conversion (FIG. 9). Compared to GCaMP3.0, GCaMP6m has five amino acid residue changes in the calmodulin moiety leaving the cpGFP backbone intact (Chen et al, 2013). This result suggests that overall structure of the GCaMP molecule is important for photo-conversion.

Green-to-Red Photoconversion of GFP

Figure 10:
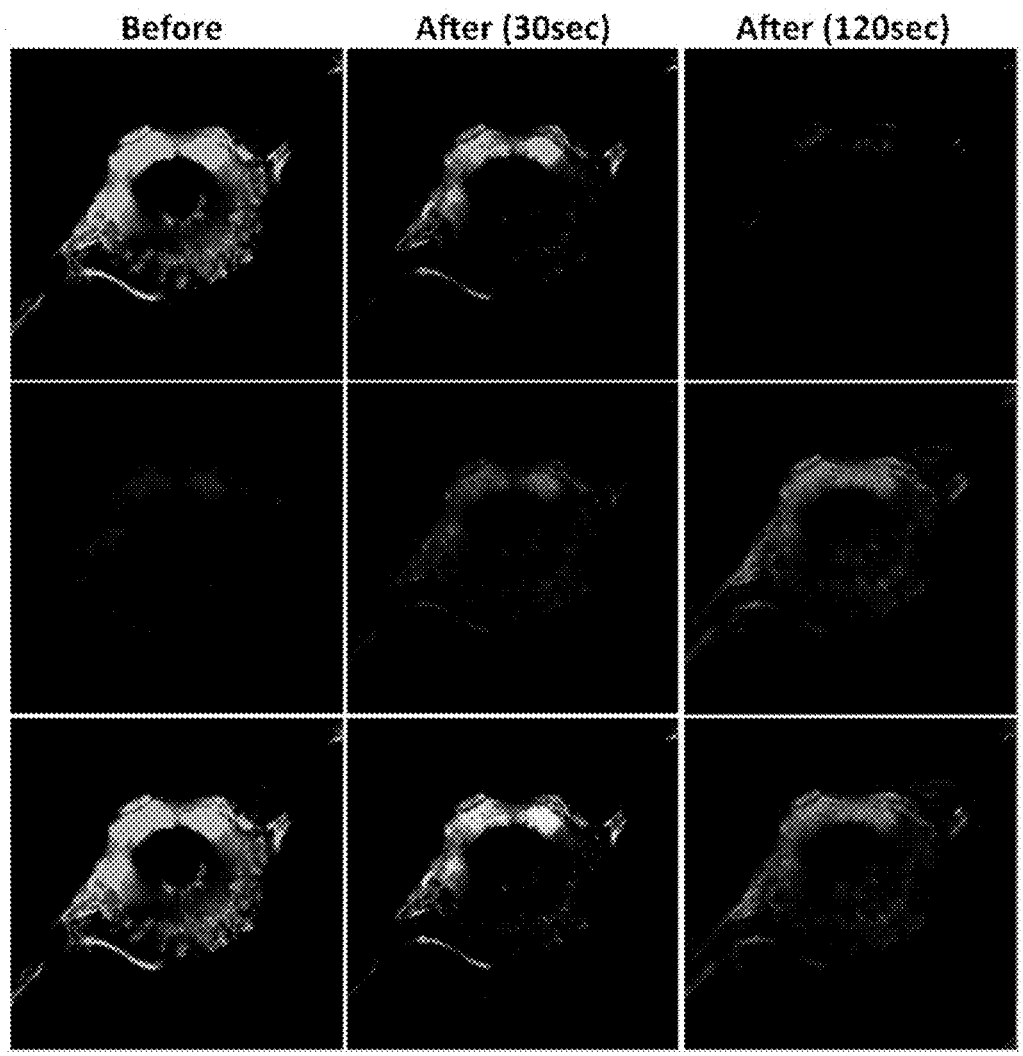
FIG. 10. GFP can be photoconverted from green to red. The brains of flies carrying GR38H02-GAL4 and UAS-CD8GFP that were dissected and subjected to light exposure resulted in green-to-red photoconversion. Top row: green fluorescent image; middle row: red fluorescent image; bottom row: merged fluorescent image.

Because GCaMP fluorescence is based on green fluorescent protein (GFP), we investigated the possibility that GFP fluorescence also undergoes light-induced green-to-red photoconversion with exposure to light. Specifically, we exposed a fly brain expressing CD8-GFP in central complex neurons under the control of GR38H02-GAL4 to blue light. We found that GFP fluorescence is also photoconverted from green to red by this exposure (FIG. 10).

Anaerobic Environment Promotes Photo-Conversion

Figure 4:
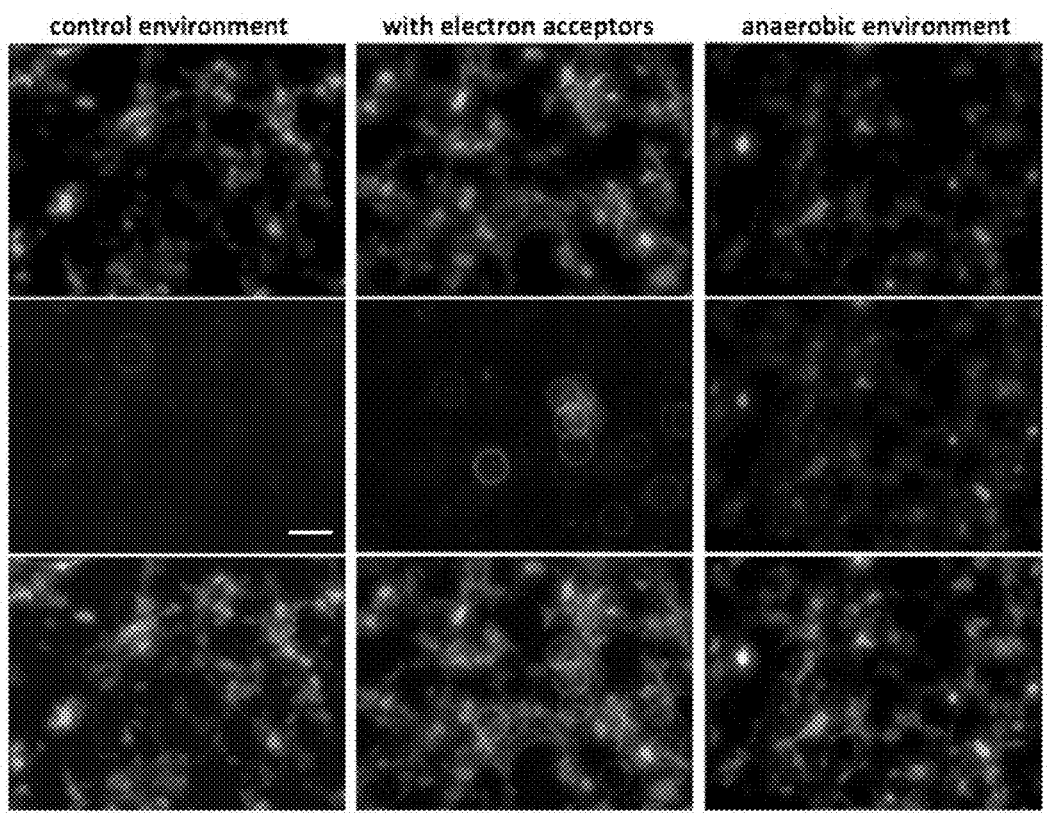
FIG. 4. The efficiency of GCaMP3.0 photo-conversion in HEK293 cells is significantly enhanced in anaerobic environment. GCaMP3.0-expressing HEK293 cells were treated under control culture condition (left column), with the presence of electron acceptor 5 mM potassium ferricyanide (middle column) or under an anaerobic condition (right column) created by exposing the cells to 30 ug/ml catalase, 4.5 mg/ml glucose and 250 ug/ml glucose oxidase for 30 min Cells were then exposed to blue light (mercury arc light passed through an Olympus 20× objective) for 2 min Green (top row), red (middle row) and merged (bottom row) fluorescent micrographs of these cells were collected with an epifluorescence microscope.

It has been reported that GFP undergoes light induced green to red emission spectrum shift (Elowitz et al, 1997; Sawin and Nurse, 1997). Two possible mechanisms, "anaerobic redding" versus "oxidative redding" were proposed to explain this phenomenon in GFP. In the first model, green-to-red fluorescence change of GFP occurs only in low oxygen environment (Jakobs et al, 2003; Takahashi et al, 2006); in the second model however, GFP was found to be efficiently converted to red fluorescent in the presence of electron acceptors irrespective to the oxygen level in the environment (Bogdanov et al, 2009; Saha et al, 2013). We asked whether either of these two mechanisms could account for the green-to-red conversion we observed in GCaMP. To this end, we expressed GCaMP3.0 in HEK293 cells, and measured their conversion efficiency under different conditions and found that green-to-red conversion of GCaMP3.0 is much more efficient in low oxygen culture condition, which is produced by the presence of oxygen depleting reagents (see methods), (FIG. 4). By contrast, the presence of electron acceptors in the culture medium of HEK293 cells expressing GCaMP3.0 had no effect on the efficiency of GCaMP3.0 photo-conversion (FIG. 4). Thus, the results suggest that anaerobic environment promotes green-to-red photo-conversion of GCaMPs.

In one embodiment, anaerobic conditions or low oxygen levels to the cells are provided so as to facilitate the green to red conversion.

Covalent Bond Cleavage of GCaMPs Upon Blue Light Exposure

We further found that brief blue light exposure of GCaMP3.0 and GCaMP6m lead to covalent bond cleavage as visualized by Western blot analysis (FIG. 5). The cleavage event occurs in the same time frame as the green-to-red photo-conversion of these GCaMPs, suggesting that the cleavage may be essential for or associated with the green-to-red photo-conversion. The precise cleavage site remains unclear. We also used anti-His antibody to probe the cleavage of GCaMP3 protein after photoconversion. This was to confirm the result we obtained with anti-GFP antibody).

Table 1 below provides a summary of some of the mutants of GCaMP 3 tested for green to red fluorescence shift.

TABLE 1

Summary of fluorescence properties of mutant GCaMP3.0

| Mutations | Green Fluorescence | Convertible to Red |
|---|---|---|
| I79T | Yes | Yes* |
| I79G | No | ND |
| V115T | Yes | No |
| V115A | Yes | No |
| V115G | No | ND |
| V115W | No | ND |
| S117A | Yes | Yes |
| T222H | No | ND |
| V225N | No | ND |

ND indicates not done
*higher conversion efficiency compared to GCaMP3.0

While this invention has been described thorough embodiments, routine modifications will be apparent to those skilled in the art and such modifications are intended to be within the scope of this disclosure.

The invention claimed is:

1. A method of labeling a selected cell or set of cells out of a group of cells comprising the steps of:
   a) providing a GCaMP molecule or a polynucleotide encoding the GCaMP molecule to the group of cells, wherein the GCaMP molecule is capable of conversion from green to red fluorescence when exposed to light of wavelength from 450 to 500 nm for a sufficient period of time; and
   b) exposing the selected cell or set of cells within the group of cells to light of wavelength from 450 to 500 nm for sufficient time to effect conversion of green fluorescence to red fluorescence in the GCaMP molecule, thereby labeling the selected cell or set of cells with red fluorescence.

2. The method of claim 1 further comprising detecting red fluorescence in the labeled cells.

3. The method of claim 1, wherein the GCaMP molecule is GCaMP3.0, GCaMP5.0, GCaMP6.0, a variant of GCaMP3.0 having at least 90% homology with the amino acid sequence of GCaMP3.0 (SEQ ID NO: 2), a variant of GCaMP5.0 having at least 90% homology with the amino acid sequence of GCaMP5.0 (SEQ ID NO: 4), or a variant of GCaMP6.0 having at least 90% homology with the amino acid sequence of GCaMP6.0 (SEQ ID NO: 6).

4. The method of claim 3, wherein the variant of GCaMP6.0 is GCaMP6f or GCaMP6s.

5. The method of claim 4, wherein the amino acid at position 79 is threonine.

6. The method of claim 1, wherein the cells in step b) are exposed for at least 2 minutes.

7. The method of claim 1, wherein the cells are labeled in vivo.

8. The method of claim 7, wherein the labeled cells are visualized in an animal over a desired period of time.

9. A method for quantitating changes of calcium levels in cells comprising the steps of:
   a) providing a GCaMP molecule or a polynucleotide encoding the GCaMP molecule to the cells, wherein the GCaMP molecule is capable of conversion from green to red fluorescence when exposed to light of wavelength from 450 to 500 nm for a sufficient period of time;
   b) exposing the cells to light of wavelength from 450 to 500 nm for sufficient time to effect conversion of green fluorescence to red fluorescence in the GCaMP molecule; and
   c) measuring changes of red fluorescence intensity over a desired period of time, wherein changes in the intensity of the red fluorescence is an indicator of changes in calcium levels in the cells.

10. The method of claim 9, wherein the GCaMP molecule is GCaMP3.0, GCaMP5.0, GCaMP6.0, a variant of GCaMP3.0 having at least 90% homology with the amino acid sequence of GCaMP3.0 (SEQ ID NO: 2), a variant of GCaMP5.0 having at least 90% homology with the amino acid sequence of GCaMP5.0 (SEQ ID NO: 4), or a variant of GCaMP6.0 having at least 90% homology with the amino acid sequence of GCaMP6.0 (SEQ ID NO: 6).

11. A method of screening for variants of GCaMPs for the ability irreversibly shift from green to red fluorescence comprising the steps of:
   a) preparing a plurality of mutants having at least 90% identity with GCaMP3.0;
   b) administering to cells the polynucleotides encoding said mutants or the polypeptides of said mutants such that they are taken up by the cells;
   c) screening the cells for green fluorescence emission upon exposure to light of wavelength of 450 to 500 nm;
   d) continuing exposing the cells in which there is green fluorescence to light of wavelength of from 450 to 500 nm for at least 30 seconds; and
   e) selecting the mutants of GCaM3.0 as desirable in which there is red fluorescence after at least 30 seconds.

12. The method of claim 11, wherein the cells are exposed in step d) for a period of at least 2 minutes.

* * * * *